US007951978B2

(12) United States Patent
Arita et al.

(10) Patent No.: US 7,951,978 B2
(45) Date of Patent: May 31, 2011

(54) PROCESS FOR PRODUCING ACROLEIN AND GLYCERIN-CONTAINING COMPOSITION

(75) Inventors: Yoshitaka Arita, Nishinomiya (JP); Hideaki Tsuneki, Ohta-ku (JP); Hiroto Kasuga, Himeji (JP); Masaki Okada, Suita (JP); Masaru Kirishiki, Suita (JP)

(73) Assignee: Nippon Shokubai Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 12/312,883

(22) PCT Filed: Nov. 28, 2007

(86) PCT No.: PCT/JP2007/072972
§ 371 (c)(1),
(2), (4) Date: May 28, 2009

(87) PCT Pub. No.: WO2008/066082
PCT Pub. Date: Jun. 5, 2008

(65) Prior Publication Data
US 2010/0105957 A1    Apr. 29, 2010

(30) Foreign Application Priority Data

Dec. 1, 2006 (JP) ................. 2006-325882
Dec. 27, 2006 (JP) ................. 2006-351654
Feb. 13, 2007 (JP) ................. 2007-031498
May 31, 2007 (JP) ................. 2007-145705
Aug. 30, 2007 (JP) ................. 2007-224734

(51) Int. Cl.
C07C 45/42 (2006.01)
C07C 45/52 (2006.01)

(52) U.S. Cl. .................. 568/484; 568/486
(58) Field of Classification Search .......... 568/486; 554/174
See application file for complete search history.

(56) References Cited

U.S. PATENT DOCUMENTS

| 5,387,720 | A | 2/1995 | Neher et al. |
| 7,531,699 | B2 | 5/2009 | Dubois |
| 2007/0167642 | A1* | 7/2007 | Oku et al. ............ 554/174 |
| 2007/0277895 | A1 | 12/2007 | Zandiyeh |
| 2008/0319233 | A1 | 12/2008 | Dubois |

FOREIGN PATENT DOCUMENTS

| JP | 63216835 A | 9/1988 |
| JP | 6192147 A | 7/1994 |
| JP | 6211724 A | 8/1994 |
| JP | 6305990 A | 11/1994 |
| JP | 2001106649 A | 4/2001 |
| JP | 2001510816 A | 8/2001 |
| JP | 200595738 A | 4/2005 |
| JP | 2005200398 A | 7/2005 |
| JP | 2005213225 A | 8/2005 |
| JP | 2006521317 A | 9/2006 |
| JP | 2006290815 A | 10/2006 |
| JP | 2007137785 A | 6/2007 |
| JP | 4041512 B2 | 11/2007 |
| JP | 4041513 B2 | 11/2007 |
| WO | 2006000735 A1 | 1/2006 |
| WO | 2006087083 A2 | 8/2006 |
| WO | 2006087084 A2 | 8/2006 |
| WO | 2006092272 A2 | 9/2006 |
| WO | 2007058221 A1 | 5/2007 |
| WO | 2007090990 A2 | 8/2007 |
| WO | 2008066082 A1 | 6/2008 |

OTHER PUBLICATIONS

Dao et al., Reactions of Model Compounds of Biomass-Pyrolysis Oils over ZSM-5 Zeolite Catalysts, Pyrolysis Oils From Biomass, Sep. 30, 1988, Chapter 27, pp. 328-341, vol. 376, American Chemical Society, U.S.A.
Tabe et al., Basic data of solid acids and bases, Kagaku Sousetsu (Chemical Review), No. 34, pp. 78-89, 1982, Chapter Society of Japan, Society Publishing Center, Japan.
Hashimoto et al., A Relationship Between Hammett Acidity Function and Activation Energy of Desorption of Ammonia, Shokubai (Catalyst), 60th CATSJ Meeting Abstracts, vol. 29, No. 6, pp. 406-409, 1987, Catalyst Society of Japan, Japan.
Sakamoto et al., Preparation of Aluminium Orthophosphates in Organic Solvents and Their Properties, Nihon Kagaku Kaishi (Jrnl of Chemical Soc of Japan Chemistry and Industrial Chemistry), No. 9, pp. 681-688, 1995, The Chemical Society of Japan, Japan.
Japanese Patent Office, Notice of Reasons for Rejection, Jun. 24, 2008, JP 2006-325882, JPO, Tokyo, Japan.
Japanese Patent Office, Decision of Rejection, Aug. 12, 2008, JP 2006-325882, JPO, Tokyo, Japan.
Japanese Patent Office, Certificate of Patent, Nov. 28, 2008, 4224097, JPO, Tokyo, Japan.
Japanese Patent Office, Notice of Reasons for Rejection, Jul. 14, 2009, JP 2007-224734, JPO, Tokyo, Japan.
Japanese Patent Office, Decision of Rejection, Oct. 6, 2009, JP 2007-224734, JPO, Tokyo, Japan.

* cited by examiner

Primary Examiner — Sikarl A Witherspoon

(57) ABSTRACT

The present invention provides a process for producing acrolein, which exhibits a prolonged catalyst life, low energy consumption, and excellent efficiency, and which is earth-conscious, and a glycerin-containing composition which can preferably be used even in this process. The process for producing acrolein is one which includes bringing a raw material gas containing glycerin gas into contact with a solid acid catalyst in a reactor, and the partial pressure of the glycerin gas in the raw material gas is set to be from 0.01 to 30 kPa. The glycerin-containing composition is for use in a process for producing acrolein using a solid catalyst and includes a fatty acid and/or a fatty acid ester, and a total mass of the fatty acid and the fatty acid ester is from 0.001% to 5% by mass, relative to the glycerin.

46 Claims, No Drawings

PROCESS FOR PRODUCING ACROLEIN AND GLYCERIN-CONTAINING COMPOSITION

This is the U.S. national phase of International Application No. PCT/JP2007/072972, filed Nov. 28, 2007, which claims priority from Japanese Patent Application Nos. 2006-325882 filed Dec. 1, 2006, 2006-351654 filed Dec. 27, 2006, 2007-031498 filed Feb. 13, 2007, 2007-145705 filed May 31, 2007, and 2007-224734 filed Aug. 30, 2007, all of which applications (the International Application and the Japanese Applications) are hereby incorporated by reference in their entireties.

TECHNICAL FIELD

The present invention relates to a process for producing acrolein by gas-phase reaction of glycerin using a solid acid catalyst with excellent productivity and also to a glycerin-containing composition which can preferably be used even in this process.

BACKGROUND ART

Biodiesel fuels produced from vegetable oils have drawn much attention as alternate fuels for fossil fuels and also in terms of low emission of carbon dioxide, and therefore, an increase in demand for them has been expected. Since the production of such biodiesel fuels is accompanied by the formation of glycerin as a by-product, it is required to make effective use of glycerin. An embodiment of making use of glycerin is to use glycerin as a raw material for acrolein.

Acrolein is a useful compound to be used as a raw material of acrolein derivatives such as 1,3-propanediol, 1,2-propanediol, methionine, acrylic acid, 3-methylpropionealdehyde, and water-absorbing resins. Japanese Patent Application Laid-Open (Kokai) No. Hei 06-192147 discloses producing 1,3-propanediol and 1,2-propanediol using acrolein obtained by dehydration of glycerin. Further, Japanese Patent Laid-open Publication (Kokai) No. 2005-213225 discloses producing acrylic acid by gas-phase oxidation of a gas-phase dehydration product of glycerin. Further, WO 2006/092272 discloses obtaining acrolein from glycerin, converting this acrolein into acrylic acid by the heretofore known gas-phase oxidation, and further producing a water-absorbing resin from this acrylic acid by the heretofore known process.

It has been well known since long ago that acrolein can be produced by dehydration of glycerin and also that a solid acid catalyst is used in this production.

Japanese Patent Laid-open Publication (Kokai) No. Hei 06-211724 discloses producing acrolein by dehydrating glycerin in gas phase by bringing a glycerin-water mixture containing from 10% to 40% by mass of glycerin into contact with a solid acid catalyst having an acid strength function $H_0$ of +2 or lower (e.g., a solid acid catalyst obtained by allowing phosphoric acid to be supported on an aluminum oxide carrier) under the condition of from 250° C. to 340° C. The feed amount of glycerin per 1 hour to the catalyst is calculated to be from 80 to 160 g/hr in Examples of this publication.

Further, WO 2006/087083 discloses a process for producing acrolein by gas-phase dehydration of glycerin using a solid strongly acidic catalyst having an acid strength function $H_0$ of from −9 to −18 and describes that the reaction temperature may be preferred to be from 250° C. to 350° C. in the catalytic gas-phase dehydration using a glycerin-water mixture having a concentration of from 10% to 50% by mass and the solid strongly acidic catalyst. The feed amount of glycerin per 1 L of the catalyst in this publication is calculated to be 230 g/hr.

In addition, with respect to a process for producing acrolein using not glycerin but propylene as a raw material, Japanese Patent Laid-Open Publication (Kohyo) No. 2006-521317 discloses a process for producing acrolein by catalytic gas-phase partial oxidation of propylene. The feed amount of propylene per 1 L of a catalyst in this process is from 90 to 160 NL and when this feed amount is converted into the feed amount of glycerin per 1 L of the catalyst, it becomes from 360 to 658 g/hr.

The above respective publications disclose gas-phase reaction of glycerin using a dilute aqueous glycerin solution and suggest using a raw material gas composed of low-concentration glycerin and high-concentration water vapor; however, none of the above respective publications describes that the partial pressure of glycerin gas in the raw material gas affects on the life of a catalyst when the feed amount of glycerin is fixed to be a constant.

When the partial pressure of glycerin is lowered in a catalytic gas-phase reaction using a solid catalyst, there are (a) a method of lowering a load on the catalyst by decreasing the feed amount of glycerin depending on the partial pressure of glycerin; and (b) a method of increasing the space velocity of the entire raw material gas while a load on the catalyst is kept constant by increasing the amount of dilution gas without changing the feed amount of glycerin. In the former method, it is assumed that both product selectivity and catalyst life may be improved, whereas in the latter method, it is assumed that even if product selectivity is improved, the effect on the improvement in catalyst life is small because a load on the catalyst is constant and rather the conversion rate of glycerin may sometimes be lowered.

When the production of acrolein on an industrial scale is assumed, in the gas-phase reaction using, as a raw material, a dilute aqueous glycerin solution as disclosed in the above respective publications, a great amount of energy is consumed to evaporate a great amount of water. Further, since acrolein, which is an aimed product, has a boiling point (i.e., 52° C.) lower than that of water, energy is further consumed for the condensation of all of water vapor produced by evaporating the raw material and water vapor generated by dehydration. In addition, after acrolein is extracted from the aqueous acrolein solution obtained by the condensation, it is required to treat a great amount of wastewater. Accordingly, even if acrolein or acrolein derivatives, which are useful compounds, are produced using, as a raw material, glycerin derived from plants which are said to be earth conscious, a process for producing acrolein, which is accompanied by mass consumption of energy and mass generation of wastes, has a problem of being difficult to say that it makes consideration to the global environment.

Further, when the production of acrolein on an industrial scale is assumed, since the feed amounts of glycerin as disclosed in the above respective publications are small, the productivity of acrolein is low. Accordingly, there is an issue that an apparatus for producing acrolein becomes large, and an improvement in the productivity thereof is desired.

WO 2006/087084 discloses a process for producing acrolein under the conditions of atmospheric pressure, gas phase, and glycerin concentration of 50% by mass or lower (i.e., glycerin concentration of 16 mol % or lower in the raw material gas at the inlet of a reactor). This process uses an aqueous glycerin solution as a raw material and supplies water at an amount greater than that of glycerin to the reactor.

Japanese Patent Laid-open Publication (Kokai) No. 2005-213225 discloses a process for producing acrolein by gas-phase dehydration of glycerin and producing acrylic acid by oxidation of acrolein. In the gas-phase dehydration, the amount of water to be added to glycerin under the conditions of atmospheric pressure and gas phase is 50% by mass or lower. Further, an inert gas such as nitrogen is added to the raw material gas to be supplied to a reactor and the concentration of the inert gas in the raw material gas is 50 mol % or higher at the inlet of the reactor and the concentration of glycerin in the raw material gas is from 10 to 14 mol %.

"Le H. Dao, Reaction of Model Compounds of Biomass-Pyrolysis Oils Over ZSM-5 Zeolite Catalysts, American Chemical Society, 1988, 376, p. 328-341" discloses a process for producing acrolein using glycerin and helium gas but no water. In this literature, the yield (percent yield) of acrolein is not clearly described; however, the yield of acrolein is insufficient.

In general, if the concentration of glycerin is increased, it is possible to improve the productivity of acrolein and make small the size of a reactor for the production of acrolein. For this reason, it is expected that fixed costs, as well as variable costs required for evaporation of the raw material, heating of the raw material, and separation and refining of acrolein, can be saved, and therefore, it is expected that an increase in the concentration of glycerin has many advantages as compared with the case of decreasing the concentration of glycerin.

When low-concentration glycerin gas is used as disclosed in WO 2006/087084, Japanese Patent Laid-open Publication (Kokai) No. 2005-213225, and American Chemical Society, there are concerns about, for example, low productivity of acrolein and an increase in facility cost because of an enlargement of the reactor size. Further, when a low-concentration aqueous glycerin solution is used as described in WO 2006/087084 and Japanese Patent Laid-open Publication (Kokai) No. 2005-213225, there is a problem that a great amount of energy is required to evaporate a great amount of water and a great amount of energy is also required to condense water vapor along with the condensation and recovery of acrolein from a gaseous product obtained. Further, when a noncondensable gas such as helium gas is used as described in American Chemical Society, acrolein is scattered at the time of condensation and recovery of acrolein from a gaseous product, and a loss of acrolein is a probable risk. In addition, it is desired to improve the yield of acrolein and the life of a catalyst.

None of WO 2006/087084, Japanese Patent Laid-open Publication (Kokai) No. 2005-213225, and American Chemical Society describes the effects of carrying out the gas-phase dehydration of glycerin under a reduced pressure condition. Further, these documents contain neither descriptions nor suggestions on the conditions of gas-phase dehydration under which the yield of acrolein is increased, the recovery efficiency of acrolein is improved, and the yield of acrolein is not lowered even if the concentration of glycerin is increased.

As described above, it is desired to improve energy consumption or other problems in the process for producing acrolein. As another problem to be improved in the production of acrolein, there is the reactivation of a catalyst, of which activity has been deteriorated. WO 2006/087083 discloses that carbonaceous substances are accumulated on a catalyst or that the activity of a catalyst is deteriorated with time; however, this publication discloses no reactivation conditions of a catalyst, of which activity has been deteriorated, and makes no reference to the relationship between the temperature of gas-phase dehydration of glycerin and the temperature of catalyst reactivation.

WO 2006/087083 describes that: (1) if the reaction temperature is lowered, the conversion rate of glycerin is decreased, but the selectivity of acrolein is improved; (2) if the contact time of glycerin and a catalyst is prolonged, the conversion rate of glycerin is improved, but the prolongation of the contact time is limited to avoid consecutive reactions and formation of by-products; and (3) the prolongation of the contact time is effective as means for making an improvement in the conversion rate of glycerin when the reaction temperature is low; however, there is no specific description on the relationship between the contact time and yield of acrolein. Further, the relationship between the feed amount of glycerin and the reaction conditions are not disclosed at all, and even if acrolein is produced at the feed amount under the reaction conditions as shown in Examples, the production efficiency of acrolein under these conditions is insufficient from an industrial point of view, and therefore, when these conditions are employed, a great amount of a catalyst and a large-size reaction apparatus are required. That is, from an economical point of view, it is desired to improve the reaction conditions.

DISCLOSURE OF THE INVENTION

It is an object of the present invention to provide a process for producing acrolein, which exhibits low energy consumption and excellent efficiency, and which makes consideration to the global environment. It is another object of the present invention to provide a process for producing acrolein by gas-phase dehydration of glycerin, which exhibits excellent yield of acrolein and prolonged catalyst life.

The present inventors have made intensive studies on a process for producing acrolein from glycerin, and as a result, they have found that the yield of acrolein, which is an aimed product, can be improved by lowering the partial pressure of glycerin gas in the raw material gas in the gas-phase dehydration of glycerin and also that the amount of carbonaceous substances accumulated on a catalyst is proportional to the partial pressure of glycerin gas even if the amount of glycerin to be brought into contact with the catalyst is the same, so that it particularly affects on the life of the catalyst. That is, the present inventors have found that in the gas-phase dehydration of glycerin with the same load on a catalyst, if the partial pressure of glycerin gas is lowered, the selectivity of acrolein is improved as well as the life of the catalyst is remarkably improved. These findings now have lead to the completion of the present invention.

The present invention provides a process for producing acrolein by bringing a raw material gas containing glycerin gas into contact with a solid acid catalyst in a reactor, wherein the partial pressure of the glycerin gas in the raw material gas is from 0.01 to 30 kPa. According to the production process of the present invention, the excellent yield of acrolein and the excellent life of the catalyst can be realized and further both the energy consumption and the wastewater amount can be decreased to make small an environmental load. The space velocity of the above glycerin gas may preferably be from 70 to 2,400 $hr^{-1}$.

To produce acrolein with the practical condition of a glycerin load on a catalyst and without lowering the yield of acrolein, the feed amount of glycerin gas per 1 L of the catalyst may be from 300 to 15,000 g/hr and the reaction temperature for producing acrolein may be from 350° C. to 460° C.

When the pressure at the inlet of a reactor is higher than 90 kPa, a contact time calculated by dividing the volume of the catalyst by the flow rate of the raw material gas per 1 second may be from 0.1 to 7.2 seconds. The pressure at the inlet of the reactor when a contact time is set to be in this range may preferably be 100 kPa or higher.

When a raw material gas having a high concentration of glycerin is used at atmospheric pressure, the yield of acrolein may sometimes be decreased as compared with the case where a raw material gas having a low concentration of glycerin. The present inventors have found that acrolein can be produced at a high yield and at the same time the life of a catalyst can be improved, even if a raw material gas having a high concentration of glycerin is used in the gas-phase dehydration of glycerin for which a prescribed reduced pressure condition is selected. That is, the pressure at the inlet of a reactor may preferably be not lower than 1 kPa and not higher than 90 kPa.

If the pressure at the inlet of a reactor is set to be not lower than 1 kPa and not higher than 90 kPa, even if a gas selected from noncondensable gases and condensable gases is not used as a dilution gas for a raw material gas, a decrease in the yield of acrolein can be suppressed. That is, it is expected to save energy consumption for evaporating and condensing water from an economical point of view and to decrease facility cost because of downsizing of the reactor. Further, it is also expected to avoid a pressure loss in the reactor and an effect of this pressure loss on the yield of acrolein. When a noncondensable gas is not used as a dilution gas, acrolein can be condensed and recovered more easily. The above descriptions mean no limit of the use of a dilution gas in the present invention. When an noncondensable gas is used as a dilution gas, the concentration of the noncondensable gas in a raw material gas at the inlet of a reactor may be 10 mol % or lower, and when a condensable gas is used as a dilution gas, the concentration of the condensable gas other than glycerin gas at the inlet of a reactor may be 60 mol % or lower. For example, the use of water vapor as a dilution gas may possibly cause an adverse effect on the ordinary dehydration of glycerin; however, if the pressure at the inlet of a reactor is in a range of not lower than 1 kPa and not lower than 90 kPa, it may be preferred from the viewpoints such as the yield of acrolein and the life of a catalyst. Incidentally, even in the process for producing acrolein according to the present invention in which the pressure at the inlet of a reactor is outside a range of not lower than 1 kPa and not higher than 90 kPa, there may also be a case where water vapor is used as a dilution gas.

In the present invention, glycerin gas may be generated by adjusting the temperature of a glycerin evaporator at 285° C. or lower. Glycerin gas is generated by a glycerin evaporator, and the glycerin gas allowed to pass through a gas flow rate control valve and a dilution gas are mixed to obtain a raw material gas. At that time, since a pressure loss at the gas flow rate control valve cannot be neglected and an inside of the glycerin evaporator is pressurized to increase the boiling point of glycerin, it is expected that the actual temperature of the evaporator is required to be 300° C. or higher. On the other hand, when the pressure at the inlet of a reactor is set to be in a range of not lower than 1 kPa and not higher than 90 kPa, the temperature of a glycerin evaporator can be lowered correspondingly to the degree of this pressure (i.e., the reduced pressure state), and therefore, it is expected that decomposition and polymerization of glycerin, and others can be suppressed at the time of evaporating glycerin.

In the process for producing acrolein according to the present invention, the above raw material gas may preferably contain water vapor as a condensable gas and the partial pressure of water vapor may preferably be at most 5 times higher than the partial pressure of the glycerin gas.

Immediately after starting the feeding of a raw material gas to a reactor, the yield of acrolein may be low and unstable (hereinafter, this period in which the yield of acrolein is low and unstable may be referred to sometimes as an "induction period"). If acrolein is not obtained at a stable yield from glycerin, the yield of acrolein becomes unstable, which is, therefore, unfavorable. At the time of continuously producing an acrolein derivative via acrolein, if the yield of acrolein becomes unstable, the feed amount of acrolein to the step of producing the derivative becomes unstable, which is, therefore, particularly unfavorable. If a tank for storing acrolein is provided, fluctuation in the feed amount of acrolein to the step of producing the derivative can be suppressed; however, since acrolein is a very unstable substance, it is desired to make short the storage time as much as possible. If the yield of acrolein is unstable, since the storage amount of acrolein in the tank has to be high, it is desired to produce acrolein at a stable yield.

The present inventors have found that the above induction period can be made short if a prescribed amount of a fatty acid and/or a fatty acid ester is added to a raw material gas. That is, if a gas containing a fatty acid and/or a fatty acid ester and having a total mass of the fatty acid and the fatty acid ester in a range of from 0.001% to 5% by mass, relative to the glycerin gas is used as the raw material gas, the yield of acrolein can be made stable and high.

The above fatty acid may be a saturated fatty acid and/or an unsaturated fatty acid, each having from 4 to 22 carbon atoms. The above fatty acid ester may be an ester of a saturated fatty acid and/or an unsaturated fatty acid, each having from 4 to 22 carbon atoms, with an alcohol having from 1 to 4 carbon atoms.

Glycerin to be used for the glycerin gas may be one produced by hydrolysis or ester exchange of fats and oils.

A process for producing acrolein, which is more excellent from an economical point of view, is the following process.

The process comprises alternately repeating an acrolein production step (1) for producing acrolein by the above process for producing acrolein and a reactivation step (2) for reactivating a solid acid catalyst having activity decreased in the step (1) by bringing a gas for reactivation containing an oxidizing gas into contact with the solid acid catalyst, wherein a highest temperature Tm(2) in the reactivation step (2) meets 300° C.$\leq$Tm(2). This temperature setting makes it possible to reactivate a solid acid catalyst.

In the reactivation step (2), carbonaceous substances are removed, which have been accumulated on the solid acid catalyst in the acrolein production step (1). If a temperature difference is large between the steps (1) and (2) at the time of producing acrolein by repeating the acrolein production step (1) and the reactivation step (2), the time and energy loss for temperature adjustment in the respective steps (1) become large, which is, therefore, unfavorable from an economical point of view. Accordingly, when the reaction temperature in the acrolein production step (1) is set to be 300° C. or higher, it has unexpectedly been found that the yield of acrolein is improved. That is, (1) since a difference between the temperature in the acrolein production step (1) and the temperature in the reactivation step (2) is small by setting the temperature of dehydration of glycerin to be 300° C. or higher in the acrolein production step (1), the time and energy loss become small between the steps (1) and (2), and therefore, acrolein can be produced at a low cost; and (2) the yield of acrolein can be improved because the temperature of dehydration of glycerin is 300° C. or higher.

An absolute value DT(12) of a difference between a temperature at the time of finishing in the acrolein production step (1) and a temperature at the time of starting in the reactivation step (2) when the acrolein production step (1) is switched to the reactivation step (2) may meet DT(12)≦100° C.

An absolute value DT(21) of a difference between a temperature at the time of finishing in the reactivation step (2) and a temperature at the time of starting in the acrolein production step (1) when the reactivation step (2) is switched to the acrolein production step (1) may meet DT(21)≦100° C.

In the process for producing acrolein comprising alternately repeating the above acrolein production step (1) and the above reactivation step (2), when the pressure at the inlet of a reactor is higher than 90 kPa, the reaction temperature in the step (1) may preferably be higher than 300° C. and not higher than 450° C., and a contact time calculated by dividing the volume of a catalyst by the flow rate of a raw material gas per 1 second may preferably be from 0.1 to 7.2 seconds. In such a short contact time, the conversion rate of glycerin is high and acrolein can be obtained at a high yield.

Further, in the process for producing acrolein comprising alternately repeating the above acrolein production step (1) and the above reactivation step (2), the feed amount of glycerin gas per 1 L of the catalyst in the step (1) may preferably be from 300 to 15,000 g/hr. Even in such a feed amount, acrolein can be obtained at a high yield.

The glycerin-containing composition according to the present invention is used as a raw material for producing acrolein by dehydration using a solid catalyst. This composition comprises a fatty acid and/or a fatty acid ester and a total mass of the fatty acid and the fatty acid ester is from 0.001% to 5% by mass, relative to glycerin.

BEST MODE FOR CARRYING OUT THE INVENTION

A process for producing acrolein according to this embodiment is one for producing acrolein by gas-phase dehydration by bringing a raw material gas containing glycerin gas into contact with a catalyst in a reactor. A reactor selected arbitrarily from fixed bed reactors, moving bed reactors, and fluidized bed reactors may be employed, and any of the fixed bed reactors which can simply produce acrolein may preferably be employed.

The gas-phase dehydration temperature in the production of acrolein according to this embodiment (hereinafter, the gas-phase dehydration temperature may be referred to sometimes as the "T1") usually indicates the preset temperature of a heating medium or others for controlling the temperature of a reactor. The temperature may appropriately be altered along with the activation change of a catalyst and the alternation of reaction conditions. The temperature may be from 200° C. to 500° C., preferably from 250° C. to 500° C., more preferably from 300° C. to 450° C., still more preferably from 330° to 440° C., further still more preferably from 350° C. to 420° C., and most preferably 350° C. to 400° C. If the reaction temperature is low, the conversion rate of glycerin is lowered and the production amount of acrolein is substantially lowered, and at the same time, an apparatus for recovering unconverted glycerin is required, which is, therefore, unfavorable. Further, if the reaction temperature is too high, the yield of acrolein is considerably lowered, which is, therefore, unfavorable.

A raw material gas comprises glycerin gas. Further, a dilution gas may be allowed to be contained in the raw material gas to adjust the concentration of glycerin. Since a dilution gas is allowed to be contained, as necessary, in the raw material gas, there is also a case where no dilution gas is allowed to be contained in the raw material gas.

The pressure of a raw material gas at the inlet of a reactor is not particularly limited. The lower limit value of the pressure of a raw material gas may appropriately be set based on a balance between the economical viewpoints such as pressure resistance of a reaction apparatus and the catalyst performance. The pressure may usually be 0.01 kPa or higher, preferably 0.1 kPa or higher, and more preferably 1 kPa or higher. The upper limit of the pressure of a raw material gas is not particularly limited so long as the raw material gas is kept in a gaseous state at the inlet of a reactor; however, it may usually be 1 MPa, preferably 500 kPa, more preferably 300 kPa, and still more preferably 200 kPa.

When a raw material gas having a high concentration of glycerin is used, the pressure of the raw material gas is not lower than 1 kPa and not higher than 90 kPa, preferably not lower than 3 kPa and not higher than 80 kPa, and more preferably not lower than 5 kPa and not higher than 70 kPa. At a pressure lower than this range, it is impossible to obtain an effect corresponding to facility costs such as a reactor with high air tightness and running costs of a production apparatus. Further, since the recovery of acrolein may sometimes become difficult, there is concern that the yield of acrolein is decreased.

The space velocity of a raw material gas containing a total amount of glycerin and a dilution gas at the inlet of a reactor (hereinafter, it may be referred sometimes to as the "space velocity" or "GHSV") may usually be from 10 to 30,000 $hr^{-1}$, preferably from 30 to 20,000 $hr^{-1}$, more preferably from 50 to 12,000 $hr^{-1}$, still more preferably from 70 to 10,000 $hr^{-1}$, further still more preferably from 100 to 5,000 $hr^{-1}$, and most preferably from 125 to 3,000 $hr^{-1}$.

The "contact time" as used herein is a value calculated by dividing the volume of a catalyst by the flow rate of a raw material gas per 1 second. That is, the contact time can be calculated by dividing the volume of a catalyst filled in a reactor by the total flow rate of a raw material gas at the inlet of the reactor. Further, the contact time can also be calculated by dividing 3,600 by GHSV. When the pressure of a raw material gas is higher than 90 kPa at the inlet of a reactor, the contact time may preferably be from 0.1 to 7.2 seconds, more preferably from 0.2 to 7.0 seconds, and still more preferably from 0.3 to 6.0 seconds.

A glycerin gas source may be any of refined products of glycerin, crude products of glycerin, and aqueous glycerin solutions. Further, it may be any of glycerin chemically synthesized from ethylene, propylene, or the like and glycerin derived from natural resources obtained by hydrolysis or ester exchange of oils and fats.

The partial pressure of glycerin gas may be 30 kPa or lower, preferably 25 kPa or lower, more preferably 20 kPa or lower, and still more preferably 15 kPa or lower. The partial pressure may be more preferred as it is lower; however, to lower the partial pressure and ensure the stable productivity of acrolein, a method such as (A) lowering the total pressure of gas in the reaction or (B) feeding together a great amount of a dilution gas other than glycerin is required. From an industrial point of view, in the above method (A), a reaction apparatus having high air tightness and durable to a reduced pressure and a large-size pressure-reducing apparatus are needed, and in the above method (B), there occur problems such as an increase in the recovery cost of acrolein produced, an increase in cost because of using a great amount of the dilution gas, and an increase in power cost accompanying an increase in pressure loss. Accordingly, the partial pressure of glycerin gas may preferably be 0.01 kPa or higher, more preferably 1.0 kPa or higher, and still more preferably 2.0 kPa or higher, from an industrial point of view.

The above "partial pressure of glycerin" is the partial pressure of glycerin in a raw material gas at the inlet of a reactor.

For example, if the mol concentration of glycerin gas in a raw material gas is 100%, the partial pressure of glycerin gas is the pressure of the raw material gas at the inlet of a reactor. Further, when a raw material gas contains components other than glycerin, it is the value calculated by multiplying the mol concentration (mol %) of glycerin gas in the raw material gas at the inlet of a reactor by the total pressure of the raw material gas at the inlet of the reactor.

The concentration of glycerin gas in a raw material gas is not particularly limited so long as the partial pressure of glycerin gas is in the above range. The concentration of glycerin gas may be from 0.1 to 100 mol % and more preferably 1 mol % or higher from economical points of view, such as a reduction in the amount of a dilution gas to be used, a decrease in the pressure loss of a reaction system, and a recovery efficiency of acrolein produced, particularly under the condition that the feed amount of glycerin (unit: g/hr) per 1 L of a catalyst is high.

When the pressure of a raw material gas is set to be not lower than 1 kPa and not higher than 90 kPa under the condition that the partial pressure of glycerin is in the above range, the concentration of glycerin gas may preferably be 20 mol % or higher, more preferably 40 mol % or higher, and still more preferably 90 mol % or higher. If the concentration of glycerin is set to be in the above range, the productivity of acrolein can be improved and the energy necessary for producing acrolein can be saved.

The "GHSV of glycerin gas" as used herein is the volume of glycerin gas based on the unit time and the unit catalyst volume. The volume of glycerin gas is the volume of glycerin gas in the standard state to be supplied to a reactor, but is not the volume of glycerin gas based on the total amount of a raw material gas at the inlet of a reactor. For example, when a raw material gas having a glycerin content of 90% by mass is fed at a flow rate of 1,000 g/hr to a reactor containing 1 L of a catalyst, the GHSV of glycerin gas is 1,000 g/hr×90% by mass/92.06 g/mol×22.4 L/mol/1 L≈219 hr$^{-1}$. The numerical value "92.06" is the molecular weight of glycerin and 1 L is the volume of the catalyst.

In comparison of two different type glycerin gases having the same partial pressure but different GHSVs, although the life of a solid acid catalyst is prolonged in the case of using glycerin gas having lower GHSV, the productivity of acrolein is decreased when the catalyst amount and the contact time are kept constant. Accordingly, taking into consideration the life of a catalyst and the size of a reactor, preferred GHSV may be set; however, from an industrial viewpoint, GHSV of glycerin gas may preferably be 70 hr$^{-1}$ or higher, more preferably 73 hr$^{-1}$ or higher, still more preferably 100 hr$^{-1}$ or higher, and most preferably 125 hr$^{-1}$ or higher. On the other hand, the upper limit of GHSV of glycerin gas may be 3,650 hr$^{-1}$. Nevertheless, when GHSV of glycerin gas is high, a reactor can be made small; however, the activity of a solid acid catalyst is rapidly deteriorated, so that the reactivation of the catalyst has to be carried out frequently. Therefore, taking into consideration a balance between the downsizing of a reactor and the activity of a solid acid catalyst, as well as low cost, GHSV of glycerin may usually be 2,400 hr$^{-1}$ or lower, preferably 1,200 hr$^{-1}$ or lower, and more preferably 600 hr$^{-1}$ or lower.

When the temperature of gas-phase dehydration in the production of acrolein is 350° C. to 460° C., the feed amount of glycerin gas may be from 300 to 15,000 g/hr, preferably from 400 to 12,000 g/hr, and more preferably from 500 to 10,000 g/hr, per 1 L of a catalyst.

When the pressure of a raw material gas at the inlet of a reactor is higher than 90 kPa, the above temperature of gas-phase dehydration, the above feed amount of glycerin gas per 1 L of a catalyst, and the above contact time have a correlative relationship. In view of performance, preferred are, for example, as follows: when the reaction temperature is not lower than 350° C. and lower than 380° C., the feed amount of glycerin gas per 1 L of a catalyst is from 300 to 3,000 g/hr and the contact time is from 0.1 to 7.2 seconds; when the reaction temperature is not lower than 380° C. and lower than 410° C., the feed amount of glycerin gas per 1 L of a catalyst is from 300 to 7,000 g/hr and the contact time is from 0.1 to 7.2 seconds; when the reaction temperature is not lower than 410° C. and lower than 440° C., the feed amount of glycerin gas per 1 L of a catalyst is from 700 to 10,000 g/hr and the contact time is from 0.1 to 3.5 seconds; when the reaction temperature is not lower than 440° C. and lower than 460° C., the feed amount of glycerin gas per 1 L of a catalyst is from 2,000 to 15,000 g/hr and the contact time is from 0.1 to 2.0 seconds. More preferably, when the reaction temperature is not lower than 350° C. and lower than 380° C., the feed amount of glycerin gas per 1 L of a catalyst is from 300 to 2,000 g/hr and the contact time is from 0.3 to 7.2 seconds; when the reaction temperature is not lower than 380° C. and lower than 410° C., the feed amount of glycerin gas per 1 L of a catalyst is from 600 to 4,000 g/hr and the contact time is from 0.3 to 6.0 seconds; when the reaction temperature is not lower than 410° C. and lower than 440° C., the feed amount of glycerin gas per 1 L of a catalyst is from 1,000 to 7,500 g/hr and the contact time is from 0.1 to 2.5 seconds; when the reaction temperature is not lower than 440° C. and lower than 460° C., the feed amount of glycerin gas per 1 L of a catalyst is from 2,500 to 10,000 g/hr and the contact time is from 0.1 to 1.0 second.

When glycerin obtained by hydrolysis or ester exchange of fats and oils is used as a glycerin gas source, if the conditions of refining glycerin are appropriately adjusted, a glycerin-containing composition having preferred contents of one or two or more types of fatty acids and/or fatty acid esters (hereinafter, referred to sometimes as the "fatty acids") can be obtained. Further, regardless of embodiments of a process for producing glycerin, a glycerin-containing composition to which appropriate amounts of the fatty acids are added may be used as a glycerin source. The method of feeding the fatty acids to the dehydration of glycerin may be (1) a method in which a glycerin-containing composition is previously prepared by mixing glycerin with the fatty acids and the composition is fed to this dehydration; and (2) a method in which glycerin and the fatty acids are separately fed to this dehydration.

The above fatty acids may be any of saturated fatty acids and unsaturated fatty acids. Further, the fatty acids are not particularly limited; however, preferred are saturated fatty acids and/or unsaturated fatty acids, each having from 4 to 22 carbon atoms, which are produced by hydrolysis or ester exchange of natural vegetable fats and oils or natural animal fats and oils. Examples of the vegetable fats and oils may include palm oil, palm kernel oil, coconut oil, soybean oil, rape seed oil, olive oil, and sesame oil. Examples of the animal fats and oils may include fish oil, tallow, lard, and sperm oil.

The above fatty acid esters are not particularly limited but may preferably be esters of the above fatty acids with lower alcohols, each having from 1 to 4 carbon atoms, or glycerin. Particularly preferred are methyl esters, ethyl esters, or monoglycerides which are esters of glycerin with fatty acids.

The content of the fatty acids as used herein is a value expressed by percent by mass of the fatty acids on the basis of the mass of glycerin. The content of the fatty acids may be from 0.001% to 5% by mass, preferably from 0.01% to 4% by mass, and more preferably from 0.05% to 2% by mass. If the content of the fatty acids is low, the induction period immediately after contact of glycerin with a solid acid catalyst is insufficiently made short, whereas if the content of the fatty acids is too high, the activity of a solid acid catalyst may rapidly be deteriorated.

The temperature of a glycerin evaporator needed to evaporate glycerin may be preferred to be decreased for the purpose of reducing a loss of glycerin because of decomposition of glycerin in the evaporator unit. When dehydration is carried out under reduced pressure conditions, since the temperature of a glycerin evaporator can be decreased depending on the degree of pressure reduction, the temperature of the glycerin evaporator may be from 120° C. to 285° C., preferably from 160° C. to 270° C., and more preferably from 190° C. to 260° C.

The partial pressure of glycerin gas in the present invention is 30 kPa or lower, and therefore, if the pressure of a raw material gas is 30 kPa or higher, a dilution gas other than glycerin is inevitably contained in the raw material gas. Further, even if the pressure of a raw material gas at the inlet of a reactor is 30 kPa or lower, a dilution gas may be contained in the raw material gas.

When a dilution gas is allowed to be contained in a raw material gas, if no adverse effect is caused on the dehydration to produce acrolein from glycerin, one or two or more kinds of gases selected from condensable gases and noncondensable gases may freely be used. It is desirable to use a condensable gas as a dilution gas, by which acrolein can easily be condensed and recovered. The condensable gas to be used as a dilution gas is a gas of a compound having a higher boiling point than that of acrolein and a boiling point of 200° C. or lower under atmospheric pressure conditions, and examples thereof may include water vapor; gases of alkane compounds such as hexane, heptane, octane, and cyclohexane; gases of aromatic compounds such as benzene, toluene, xylene, mesitylene, and ethylbenzene. On the other hand, the noncondensable gas is a gas of a compound or elementary substance, each having a boiling point of 0° C. or lower under atmospheric pressure conditions, and examples thereof may include nitrogen gas, carbon dioxide gas, oxygen-containing gases such as air, and rare gases such as helium.

After recovery of acrolein from an acrolein composition, which is obtained by gas-phase dehydration of glycerin, by absorption or condensation of a solvent and others, part or all of dilution gas components may be recycled as a dilution gas. Further, after the synthesis of an acrolein derivative such as acrylic acid from acrolein and the subsequent extraction of the resultant acrolein derivative by absorption or condensation, part or all of dilution gas components may be recycled as a dilution gas.

When dehydration is carried out under reduced pressure conditions, the concentration of a dilution gas in a raw material gas is as follows, so long as it is in the respective concentration ranges depending on the type of dilution gas as described below. The noncondensable gas may be in a concentration of 10 mol % or lower, preferably 8 mol % or lower, and more preferably 5 mol % or lower. The condensable gas may be in a concentration of 80 mol % or lower, preferably 80 mol % or lower, more preferably 40 mol % or lower, and still more preferably 10 mol % or lower. If a noncondensable gas is adjusted to a concentration in the above range, energy for heating or cooling a gas can be saved and scattering loss at the time of recovering acrolein can be decreased, which is, therefore, favorable. Further, if a condensable gas is adjusted to a concentration in the above range, energy can be saved in the same manner as that in the case of a noncondensable gas, as well as the cost of separating a dilution gas can be reduced, which is, therefore, favorable.

Water vapor has advantageous effects on the life of a solid acid catalyst and the yield of acrolein, and therefore, water vapor can preferably be used as a dilution gas. In this case, the concentration of water vapor is not particularly limited; however, from the viewpoints such as heat for evaporating water, heat for condensing water vapor in dehydration products, and treatment of wastewater, the concentration of water vapor may preferably be at most 5 times, more preferably at most 4 times, higher than the concentration (mol %) of glycerin gas in a raw material gas. Water vapor can be allowed to be contained in a raw material gas by evaporating an aqueous glycerin solution or mixing glycerin gas with water vapor.

When a noncondensable non-oxidizing gas such as nitrogen is used as a dilution gas, the partial pressure of such a gas is not particularly limited so long as the partial pressure of glycerin gas becomes in a range of from 0.01 to 30 kPa. The partial pressure of the above noncondensable non-oxidizing gas may usually be at most 100 times, preferably at most 50 times, more preferably at most 20 times, still more preferably at most 10 times, and further still more preferably at most 5 times higher than the partial pressure of glycerin gas.

When an acrolein-containing gas produced by dehydration is successively used for producing an acrolein derivative such as acrylic acid after part or all of water and others, which are components, each having a boiling point higher than that of acrolein, are removed, as necessary, or when acrolein produced by dehydration is recovered, the recovery efficiency in the step of recovering acrolein, the types and amounts of dilution gas components, and their combination may appropriately be adjusted in accordance with the conditions of producing the acrolein derivative.

When an oxidizing gas such as oxygen is contained in a dilution gas, accumulation of carbonaceous substances on a solid acid catalyst is decreased. Further, there may be obtained an effect of suppressing deterioration in the activity of a solid acid catalyst. However, if the amount of oxidizing gas is too great, the yield of acrolein may be decreased because of combustion reaction, which is, therefore, unfavorable. When oxygen is used as an oxidizing gas, the amount of oxygen may preferably be at most either a lower value of not higher than 20 mol % (more preferably not higher than 15 mol %) in a raw material gas at the inlet of a reactor or at most 3.5 times higher than the partial pressure of glycerin gas.

Examples of the solid acid catalyst may include (a) crystalline metallosilicates, (b) metal oxides, (c) clay minerals, (d) mineral acids supported on inorganic carriers, and (e) metal salts of phosphoric acid or sulfuric acid, and those obtained by allowing these metal salts to be supported on inorganic carriers such as α-alumina, silica, zirconium oxide, and titanium oxide. Examples of the crystalline metallosilicates as the above (a) may include those which contain, as T atom or atoms, one or two or more kinds of elements selected from Al, B, Fe, Ga, and others, and which have crystal structures such as LTA, CHA, FER, MFI, MOR, BEA, and MTW. Examples of the above metal oxides as the above (b) may include simple metal oxides such as $Al_2O_3$, $TiO_2$, $ZrO_2$, $SnO_2$, and $V_2O_5$; and composite oxides such as $SiO_2$—$Al_2O_3$, $SiO_2$—$TiO_2$, $TiO_2$—$WO_3$, and $WO_3$—$ZrO_2$. Examples of the clay minerals as the above (c) may include bentonite, kaolin, and montmorillonite. Examples of the mineral acids supported on inorganic carriers as the above (d) may include those obtained by allowing mineral acids such as phosphoric acid and sulfuric acid to be supported on inorganic carriers such as α-alumina, silica, zirconium oxide, and titanium oxide. Examples of the metal salts of phosphoric acid and sulfuric acid as the above (e) may include $MgSO_4$, $Al_2(SO_4)_3$, $K_2SO_4$, $AlPO_4$, and $Zr_3(PO_4)_4$.

Further, other examples of the solid acid catalyst may include catalysts disclosed in WO 2006/087083 and WO 2006/087084 (e.g., zirconium oxide supporting phosphoric acid, sulfuric acid, or tungsten oxide).

In the dehydration of glycerin and the reactivation treatment of a solid acid catalyst, the solid acid catalyst is exposed to a high temperature oxidizing atmosphere or a high temperature reducing atmosphere. Therefore, it may be preferred to select a solid acid catalyst with high stability from the above examples. Examples of the solid acid catalyst with high stability may include crystalline metallosilicates, metal oxides, and clay minerals.

When a crystalline metallosilicate is used as a solid acid catalyst, HZSM5 containing Al as T atom and having MFI structure is a particularly preferred catalyst. HZSM 5 is a strongly acidic metallosilicate having values around −9 and −16 in terms of acid strength function $H_0$ of Hammett (see "Kenji Hashimoto et al., Catalyst (1987), Vol. 29, No. 6, p. 406-409").

When a metal oxide is used as a solid acid catalyst, aluminum phosphate is a particularly preferred catalyst. Aluminum phosphate has acid strength function $H_0$ of Hammett in a range of +1.5 to +4.8 and shows weak acidity, although it differs based on the preparation method for obtaining this catalyst or the crystal system of this catalyst (see "Kiyoko Sakamoto et al., Journal of the Chemistry Society of Japan (1995), 9, p. 681-688"). Aluminum phosphate having a crystal structure such as tridymite type, cristobalite type, or quartz type may preferably be selected. When aluminum phosphate having a crystal structure of tridymite type or cristobalite type is selected as a solid acid catalyst, a decrease in the yield of acrolein with time and the deposition of carbonaceous substances on this catalyst can be suppressed. On the other hand, when aluminum phosphate having a crystal structure of quartz type is selected as a solid acid catalyst, the amount of carbonaceous substances deposited on this catalyst is small.

The crystalline aluminum phosphate can be obtained by preparing a metavariscite ($AlPO_4 \cdot 2H_2O$) from orthophosphoric acid and aluminum hydroxide, adding an aqueous phosphoric acid solution to the resultant metavariscite, successively drying the mixture, and treating the dried product with a solvent. It has been known that if the solvent to be used at this time is appropriately selected, the tridymite type, cristobalite type, or quartz type can be produced selectively. Further, if a precipitate obtained by adding ammonia water to an aqueous solution containing orthophosphoric acid and aluminum nitrate dissolved therein is calcinated at 1,000° C. or higher, the tridymite type crystal can be prepared.

When the activity of a catalyst is deteriorated, if the catalyst is brought into contact with a gas for reactivation at a high temperature, the catalyst can be reactivated. The "gas for reactivation" as used herein is a gas containing an oxidizing gas such as oxygen. A method of bringing a catalyst into contact with a gas for reactivation containing an oxidizing gas is not particularly limited, but may include a method of bringing a catalyst extracted from a reactor into contact with a gas for reactivation; and a method of allowing a gas for reactivation through a reactor which is the same as a reactor in which the dehydration of glycerin is carried out. The latter method of allowing a gas for reactivation through a reactor is recommended in the case of producing acrolein using a fixed bed reactor because it does not require any work of extracting the catalyst out of the reactor or re-filling the reactor with the catalyst.

When oxygen is used as an oxidizing gas in reactivation of a catalyst, the use of oxygen in air is inexpensive. Further, an inert gas such as nitrogen, carbon dioxide, or water vapor may be supplied together with oxygen. Particularly, when there is concern that drastic heat generation occurs by the contact of air with a catalyst, it is recommended to use an inert gas for adjusting the concentration of oxygen. Before and after the catalyst reactivation treatment, purging with an inert gas such as nitrogen may be carried out for the purpose of removing extra organic substances remaining in the reactivation treatment system and oxygen incorporated at the time of filling the catalyst.

When a catalyst is reactivated, it may be preferred to reactivate the catalyst according to the following reactivation step (2). In the following explanation of the reactivation step (2), the "step of producing acrolein by gas-phase dehydration of glycerin" may be referred to sometimes as the "acrolein production step (1)."

The reactivation step (2) is carried out by bringing a catalyst, of which activity has been deteriorated by catalytic gas-phase dehydration of glycerin, into contact with a gas for reactivation at a high temperature. When the acrolein production step (1) is feeding glycerin gas by allowing a raw material gas to pass through a fixed bed reactor, the reactivation step (2) can be carried out by changing the gas to be fed into the reactor with a gas for reactivation. Unless otherwise indicated, catalyst reactivation in a fixed bed reactor will be described below.

The highest temperature Tm in the reactivation step (2) is the highest temperature when from a catalyst, of which activity has been deteriorated by the accumulation of carbonaceous substances in the acrolein production step (1), these accumulated substances are removed using a gas for reactivation. Tm usually indicates a preset highest temperature of a heating medium for controlling the temperature of a reactor in which the catalyst is to be reactivated. For example, when the temperature is controlled to be constant during catalyst reactivation, the controlled temperature is regarded as Tm, and when the controlled temperature in the reactivation step (2) is increased or decreased for the purpose of controlling the heat generation of a catalyst layer accompanying the removal of carbonaceous substance during the reactivation step (2), the highest preset temperature during the reactivation step (2) is regarded as Tm.

For the purpose of completely removing carbonaceous substances accumulated on a catalyst in the acrolein production step (1), it is required to set Tm at 300° C. or higher. Tm may preferably be 330° C. or higher and more preferably 350° C. or higher. If Tm is lower than 300° C., the removal of carbonaceous substances becomes insufficient, and therefore, there may occur problems such as insufficient recovery of catalyst activity and rapid deterioration of catalyst activity. Tm may be set to be high, if the temperature does not cause thermal deterioration of a catalyst; however, changing the temperature of a reactor every time for the acrolein production step (1) and the reactivation step (2) is not unfavorable from an economical point of view because energy for increasing the temperature may be lost as well as it takes time to increase or decrease the temperature. Accordingly, the temperature in the reactivation step (2) may be preferred to be a temperature which makes it possible to carry out the reactivation of a catalyst and which is as close as possible to the temperature in the dehydration of glycerin.

When oxygen is used as an oxidizing gas in a gas for reactivation, the use of air is inexpensive. The gas for reactivation may be one diluted with an inert gas such as nitrogen, carbon dioxide, or water vapor. In particular, when there is concern that drastic heat generation occurs by the contact of air with a catalyst, it is recommended to control the concentration of oxygen in a gas for reactivation with an inert gas. In addition, before allowing a gas for reactivation to pass through a reactor, for example, treatment of purging organic substances remaining in the reactor may be carried out by allowing a non-oxidizing gas such as nitrogen or water vapor to pass through the reactor.

In the reactivation step (2), for the purpose of burning to remove carbonaceous substances from a catalyst while preventing the heat deterioration of the catalyst by heat generation and the damage of a reactor by drastic local heat generation, it is required to control the temperature in the reactivation step (2) for reducing the amount of heat generation. Accordingly, as the amount of carbonaceous substances is higher, it takes a longer time to carry out the reactivation treatment of a catalyst.

For the purpose of reducing the amount of heat generation, there is mentioned, for example, a method of adjusting the concentration of oxygen contained in a gas for reactivation, SV, and treatment temperature. The oxygen concentration and others may appropriately be selected from ranges of oxygen concentration extending from 0.01 to 21 mol %, SV extending from 100 to 100,000 $hr^{-1}$, and treatment temperature extending from 200° C. to 550° C. For the purpose of preventing accidents such as irreversible heat deterioration of a catalyst and damage of a reactor by unexpected drastic heat generation, it is recommended to employ, for example, a method of gradually increasing treatment temperature while confirming the temperature of a catalyst layer or a method of increasing the concentration of oxygen while similarly confirming the temperature of a catalyst layer.

The "temperature at the time of starting the acrolein production step (1)" means the temperature T1 at the time of switching the reactivation step (2) to the acrolein production step (1). That is, the temperature at the time of starting is T1 at the time of starting the feeding of glycerin gas to a catalyst in the acrolein production step (1). The "temperature at the time of finishing the acrolein production step (1)" means the temperature T1 at the time of switching the acrolein production step (1) to the reactivation step (2). That is, the temperature at the time of finishing is T1 at the time of stopping the feeding of glycerin gas to the catalyst in the acrolein production step (1). Further, the "temperature at the time of starting the reactivation step (2)" means the temperature at the time of switching the acrolein production step (1) to the reactivation step (2). That is, the temperature at the time of starting is the temperature at the time of starting the contact of a catalyst with a gas for reactivation. The "temperature at the time of finishing the reactivation step (2)" means the temperature at the time of stopping the contact of the catalyst with the gas for reactivation.

When acrolein is produced under the presence of an oxidizing gas in the acrolein production step (1), the oxidizing gas (e.g., oxygen) to be used in the reactivation step (2) may continuously be used in the acrolein production step (1). In this case, the temperature at the time of finishing in the reactivation step (2) means the temperature at the time of starting the feeding of glycerin to the catalyst. That is, the temperature at the time of finishing in the reactivation step (2) and the temperature at the time of starting in the acrolein production step (1) are the same as each other.

The phrase "at the time of switching the acrolein production step (1) to the reactivation step (2)" may include switching to the reactivation step (2), which has been previously planned based on the performance of a catalyst, and the case where the contact of glycerin with a catalyst is stopped by an unplanned trouble in the acrolein production step (1) because of a trouble such as electric power failure and the reactivation step (2) is then carried out after recovery from the trouble.

The term "DT(12)" is the absolute value of a difference between the temperature at the time of finishing in the acrolein production step (1) and the temperature at the time of starting in the reactivation step (2) carried out thereafter. The term "DT(21)" is the absolute value of a difference between the temperature at the time of finishing in the reactivation step (2) and the temperature at the time of starting in the acrolein production step (1) carried out thereafter. For example, when the acrolein production step (1) is started at 330° C. and finished at 350° C., the reactivation step (2) is then started at 300° C. and finished at 360° C., and the acrolein production step (1) is repeated again, DT(12)=|350° C.-300° C.|=50° C., and DT(21)=|360° C.-330° C.|=30° C. That is, the temperature during the respective steps is irrelevant to DT(12) and DT(21), and the absolute value of a difference between the temperature at the time of finishing in the previous step and the temperature at the time of starting in the next step becomes an index for DT(12) and DT(21). It is indicated that a difference in temperature between the steps is smaller as DT(12) and DT(21) are smaller, and if this difference is small, an energy loss accompanying the switching of the steps can be made low and a waiting time accompanying the switching of the steps can be made short, and therefore, acrolein can be produced at a low cost. DT(12) and DT(21) may preferably be 100° C. or lower, more preferably 80° C. or lower, still more preferably 60° C. or lower, and most preferably 50° C. or lower.

EXPERIMENTAL EXAMPLES

Experimental Examples will be described below.

The following will describe methods of calculating the conversion rate of glycerin, the yield of acrolein, and the amount of carbonaceous substances accumulated in Experimental Examples.

Conversion Rate of Glycerin and Yield of Acrolein:

The qualitative and quantitative analyses of the flowing-out material from a reactor as described below were carried out by gas chromatography (GC). The conversion rate and the yield of acrolein were calculated from the results of the quantitative analysis and the following formulae (1) and (2).

Formula (1): Conversion rate (%)=(1−number of moles for glycerin in flowing-out material/number of moles for glycerin fed into reactor for 30 minutes)×100     [Formula 1]

Formula (2): Yield of acrolein=(number of moles for acrolein/number of moles for glycerin fed into reactor for 30 minutes)×100     [Formula 2]

Amount of Carbonaceous Substances Accumulated

The amount of carbonaceous substances deposited on a catalyst after the production of acrolein was measured by thermogravimetric-differential thermal analysis (TG-DTA). In the TG-DTA, a catalyst was placed under the flow of air, and heated from room temperature to 600° C. at a speed of 10° C./min, and kept at 600° C. for 20 minutes. The amount of carbonaceous substances accumulated was calculated based on the following formula (3).

Formula (3): Amount of carbonaceous substances accumulated (%)=(mass decreased in TG-DTA/ mass of catalyst after TG-DTA)×100     [Formula 3]

According to the following Catalyst Preparation Examples A and B, catalyst A and B were prepared. Using the catalyst A or B, acrolein was produced according to the following Experimental Examples 1 to 31.

Catalyst Preparation Example A

First, 49 g of 85% by mass orthophosphoric acid was mixed with a solution containing 160 g of aluminum nitrate nonahydrate and 800 g of distilled water. Then, 96.7 g of 28% by mass ammonia water was added dropwise to the mixed solution over about 50 minutes (from the beginning of the dropwise addition, a white precipitate was formed), and the mixed solution was stirred for 1 hour. Then, the solid substance (precipitate) was separated from the mixed solution by suction filtration and washed. The washing was carried out by mixing the solid substance with 800 g of ion exchanged water, stirring the mixture for 1 hour, and then allowing the mixture to stand still for 1 hour, after which the solid substance was separated by suction filtration. The solid substance was subjected to the washing operation repeated three times, and then dried overnight under the conditions of 120° C. and air atmosphere. The solid substance was calcinated under the conditions of 1,200° C. and air atmosphere for 3 hours. The resultant solid substance was crushed and classified into sizes of from 0.7 to 1.4 mm to obtain the catalyst A.

Catalyst Preparation Example B

First, 0.58 g of NaOH was dissolved in 15.00 g of distilled water, and 1.95 g of $NaAlO_2$ (available from Asada Chemical Industry Co., Ltd.; purity: 86.8% by mass) was successively dissolved in the distilled water, and 10.15 g of an aqueous solution containing 40% by mass of tetra-n-propylammonium hydroxide was further added to the distilled water. Then, distilled water was added to the resultant solution to prepare an impregnating solution having a total volume of 30 mL. Then, silica beads ("CARiACT Q-50", available from Fuji Silysia Chemical Ltd.; from 10 to 20 meshes; average fine pore diameter: 50 nm) were used as a silica formed product, and 30 g of the silica beads dried at 120° C. for 1 day were impregnated with the impregnating solution for 1 hour. Then, the silica beads were dried on an evaporating dish placed on a hot water bath at 100° C. and further dried at 80° C. under a nitrogen stream for 5 hours, thereby allowing Na, Al, and a crystallization agent necessary for crystallization to be supported on the silica beads to obtain a crystalline methanosilicate precursor. The resultant precursor was placed in the hollow position of a jacket-bearing crucible made of polytetrafluoroethylene and having a capacity of 100 mL, and 1.00 g of distilled water was put in the bottom position of the crucible. This crucible was allowed to stand still in an electric furnace at 180° C. for 8 hours to crystallize the precursor. The solid substance obtained by the crystallization was immersed in 300 g of an aqueous solution containing 1 mol/L ammonium nitrate at 60° C., and the mixture was stirred for 1 hour, after which the supernatant solution was discarded. This operation was repeated more than once. Then, the solid substance was washed with water. The solid substance was calcinated in an air stream at 540° C. for 3.5 hours. The catalyst B, which was HZSM5, was obtained by this calcination.

Process for Producing Acrolein in Experimental Examples 1 to 31:

A stainless steel reaction tube (having an inner diameter of 10 mm and a length of 500 mm) filled with 15 mL of a catalyst was prepared as a fixed bed reactor. This reactor was immersed in a molten salt bath at 360° C., and a raw material gas having a prescribed concentration of glycerin was then fed into the reactor. After the raw material gas was fed into the reactor for a prescribed time, a gas flowing out of the reactor was condensed by cooling and collected for 30 minutes (hereinafter, the "material condensed by cooling the collected flowing-out gas" is referred to as the "flowing-out material"). As a result of the qualitative analysis by GC, glycerin, acrolein, and 1-hydroxyacetone were detected.

Experimental Example 1

Acrolein was produced under the conditions of the catalyst A, a raw material gas of glycerin:water:nitrogen=4 mol %:20 mol %:80 mol %, and GHSV of the raw material gas of 4,220 $hr^{-1}$. The pressure of the raw material gas at the inlet of the reactor was 106.8 kPa. The result is shown in Table 1 below.

Experimental Examples 2 to 18

Acrolein was produced in the same manner as described in Experimental Example 1, except that the conditions of Experimental Example 1 were changed as shown in Table 1 below. The conditions of acrolein production and the results in Experimental Examples 2 to 18 are shown in Tables 1 and 2 below.

Experimental Example 19

Acrolein was produced under the conditions of the catalyst B, the partial pressure of glycerin gas of 33.0 kPa, the partial pressure of water vapor of 42.3 kPa, the partial pressure of $N_2$ of 27.8 kPa, and the GHSV of glycerin gas of 337.6 $hr^{-1}$. The results are shown in Table 1 below.

Experimental Examples 20 to 28

Acrolein was produced using the catalyst B. The conditions of acrolein production the results in Experimental Examples 20 to 28 are shown in Table 3 below.

Experimental Example 29

Acrolein was produced in the same manner as described in Experimental Example 1, except the following matter. There was used a reactor equipped with a vacuum pump and a vacuum controller, both attached to the outlet of the reactor, enabling to adjust the pressure of a raw material gas at the inlet of the reactor. The inlet pressure of the reactor was changed from 106.5 kPa to 63.1 kPa; the pressure of glycerin gas at the inlet of the reactor was changed from 4.3 kPa to 27.7 kPa; the pressure of water vapor at the inlet of the reactor was changed from 21.4 kPa to 35.4 kPa; and GHSV of glycerin gas was changed from 4,220 $hr^{-1}$ to 403 $hr^{-1}$, respectively. The partial pressure ratio of water vapor to glycerin gas was 1.28, and GHSV of glycerin gas was 177 $hr^{-1}$. The results for a period extending from 0.5 to 1.0 hours after the start of the feeding of the raw material gas and for a period extending from 5.5 to 6.0 hours after the start of the feeding of the raw material gas are shown in Table 4 below.

Experimental Examples 30 and 31

Acrolein was produced under the conditions of acrolein production as shown in Table 4, while the catalyst A was changed to the catalyst B in Experimental Example 29. The conditions were the same as those in Experimental Example 1, except the above conditions. The conditions of acrolein production and the results in Experimental Examples 30 and 31 are shown in Table 4 below.

TABLE 1

| | | Experimental Examples | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 19 |
| Catalyst | | Catalyst A | | | | | | | | | | | | |
| Partial pressure of GLY gas (kPa) | | 4.3 | 8.5 | 16.5 | 4.2 | 8.5 | 16.5 | 4.3 | 8.5 | 16.6 | 8.6 | 16.7 | 27.6 | 33.0 |
| Partial pressure of water vapor (kPa) | | 21.4 | 41.9 | 82.6 | 14.4 | 28.2 | 56.6 | 5.4 | 10.5 | 20.8 | 10.7 | 20.8 | 35.3 | 42.3 |
| Partial pressure of nitrogen (kPa) | | 79.7 | 54.5 | 4.1 | 87.4 | 67.9 | 29.8 | 96.9 | 86.1 | 66.4 | 87.4 | 66.5 | 39.2 | 27.8 |
| Partial pressure at inlet of reactor (kPa) | | 106.8 | 104.9 | 103.2 | 106.1 | 104.4 | 102.9 | 106.5 | 105.0 | 103.8 | 106.6 | 103.9 | 102.1 | 103.1 |
| Partial pressure of water vapor/ partial pressure of GLY (kPa/kPa) | | | 5.0 | | | 3.4 | | | 1.25 | | | 1.28 | | |
| GHSV of raw material gas (hr$^{-1}$) | | 4,220 | 2,110 | 1,055 | 4,220 | 2,110 | 1,055 | 4,220 | 2,110 | 1,055 | 4,220 | 2,110 | 640 | 1,055 |
| GHSV of GLY (hr$^{-1}$) | | | | | | 170 | | | | | | 338 | 173 | 338 |
| From 0.5 to 1.0 hr | GLY conversion rate (%) | 100.0 | 100.0 | 100.0 | 100.0 | 100.0 | 100.0 | 100.0 | 100.0 | 100.0 | 100.0 | 100.0 | 100.0 | 100.0 |
| | ACR yield (%) | 71.8 | 71.7 | 64.6 | 64.8 | 67.4 | 67.3 | 69.5 | 68.8 | 58.1 | 68.6 | 64.2 | 64.7 | 70.0 |
| From 2.5 to 3.0 hrs | GLY conversion rate (%) | 100.0 | 100.0 | 100.0 | 100.0 | 100.0 | 100.0 | 100.0 | 100.0 | 100.0 | 100.0 | 100.0 | 100.0 | 100.0 |
| | ACR yield (%) | 74.2 | 71.0 | 65.2 | 69.5 | 73.9 | 67.6 | 68.7 | 70.0 | 65.1 | 64.6 | 64.3 | 66.5 | 56.1 |
| From 4.5 to 5.0 hrs | GLY conversion rate (%) | 100.0 | 100.0 | 100.0 | 100.0 | 100.0 | 100.0 | 100.0 | 100.0 | 100.0 | 100.0 | 100.0 | 100.0 | 100.0 |
| | ACR yield (%) | 72.5 | 71.8 | 68.5 | 71.5 | 71.4 | 67.8 | 67.1 | 71.0 | 68.8 | 64.9 | 61.5 | 64.6 | 54.2 |
| From 6.5 to 7.0 hrs | GLY conversion rate (%) | 100.0 | 100.0 | 100.0 | 100.0 | 100.0 | 100.0 | 100.0 | 100.0 | 100.0 | 100.0 | 100.0 | 100.0 | 100.0 |
| | ACR yield (%) | 73.0 | 72.9 | 67.6 | 71.4 | 73.8 | 69.1 | 65.1 | 70.9 | 68.0 | 66.9 | 64.0 | 66.5 | 47.6 |
| Amount of carbonaceous substances (% by mass) | | 10 | 13 | 19 | 9 | 13 | 20 | — | — | — | 18 | 18 | 18 | 23 |

GLY: glycerin
ACR: acrolein

TABLE 2

| | | Experimental Examples | | | | | |
|---|---|---|---|---|---|---|---|
| | | 13 | 14 | 15 | 16 | 17 | 18 |
| Catalyst | | Catalyst A | | | | | |
| Partial pressure of GLY gas (kPa) | | 5.2 | 7.2 | 10.2 | 15.3 | 20.4 | 27.5 |
| Partial pressure of water vapor (kPa) | | 0.0 | 0.0 | 0.0 | 0.0 | 0.0 | 0.0 |
| Partial pressure of nitrogen (kPa) | | 98.2 | 95.7 | 91.9 | 86.7 | 81.6 | 74.3 |
| Partial pressure at inlet of reactor (kPa) | | 103.4 | 102.9 | 102.1 | 102 | 102 | 101.8 |
| Partial pressure of water vapor/ partial pressure of GLY (kPa/kPa) | | 0 | | | | | |
| GHSV of raw material gas (hr$^{-1}$) | | 3,400 | 2,430 | 1,700 | 1,133 | 850 | 630 |
| GHSV of GLY (hr$^{-1}$) | | 170 | | | | | |
| From 0.5 to 1.0 hr | GLY conversion rate (%) | 100.0 | 100.0 | 100.0 | 100.0 | 100.0 | 100.0 |
| | ACR yield (%) | 76.3 | 71.3 | 62.5 | 64.8 | 61.1 | 56.0 |
| From 2.5 to 3.0 hrs | GLY conversion rate (%) | 100.0 | 100.0 | 100.0 | 100.0 | 100.0 | 100.0 |
| | ACR yield (%) | 74.1 | 69.4 | 65.0 | 62.6 | 62.0 | 63.7 |
| From 4.5 to 5.0 hrs | GLY conversion rate (%) | 100.0 | 100.0 | 100.0 | 100.0 | 100.0 | 100.0 |
| | ACR yield (%) | 71.1 | 71.9 | 61.5 | 62.6 | 62.9 | 61.7 |
| From 6.5 to 7.0 hrs | GLY conversion rate (%) | 100.0 | 100.0 | 100.0 | 100.0 | 100.0 | 100.0 |
| | ACR yield (%) | 71.7 | 68.1 | 62.5 | 60.4 | 62.8 | 60.5 |
| Amount of carbonaceous substances (% by mass) | | 10 | 9 | 13 | 15 | 18 | 17 |

GLY: glycerin
ACR: acrolein

TABLE 3

| | | Experimental Examples | | | | | | | | |
|---|---|---|---|---|---|---|---|---|---|---|
| | | 20 | 21 | 22 | 23 | 24 | 25 | 26 | 27 | 28 |
| Catalyst | | | | | | Catalyst B | | | | |
| Partial pressure of GLY gas (kPa) | | 8.4 | 16.8 | 4.3 | 8.4 | 16.5 | 4.3 | 8.4 | 16.7 | 27.6 |
| Partial pressure of water vapor (kPa) | | 42.1 | 83.1 | 15.0 | 29.5 | 57.8 | 5.3 | 10.5 | 20.9 | 35.2 |
| Partial pressure of nitrogen (kPa) | | 54.8 | 4.1 | 87.7 | 67.5 | 28.9 | 96.8 | 86.1 | 66.8 | 40.5 |
| Partial pressure at inlet of reactor (kPa) | | 105.3 | 103.9 | 106.9 | 105.4 | 103.2 | 106.4 | 105 | 104.3 | 103.2 |
| Partial pressure of water vapor/ Partial pressure of GLY (kPa/kPa) | | 5.0 | | | 3.5 | | | 1.2 | | 1.3 |
| GHSV of raw material gas (hr$^{-1}$) | | 2,110 | 1,055 | 4,220 | 2,110 | 1,055 | 4,220 | 2,110 | 1,055 | 632 |
| GHSV of GLY (hr$^{-1}$) | | | | | | 169 | | | | |
| From 0.5 to 1.0 hr | GLY conversion rate (%) | 100.0 | 100.0 | 100.0 | 100.0 | 100.0 | 100.0 | 100.0 | 100.0 | 100.0 |
| | ACR yield (%) | 74.8 | 64.8 | 70.5 | 72.6 | 67.9 | 59.8 | 68.6 | 62.8 | 62.2 |
| From 11.5 to 12 hrs | GLY conversion rate (%) | 100.0 | 100.0 | 100.0 | 100.0 | 100.0 | 100.0 | 95.1 | 100.0 | 91.9 |
| | ACR yield (%) | 78.3 | 63.3 | 69.8 | 69.0 | 52.1 | 65.6 | 59.1 | 58.2 | 58.6 |
| From 23.5 to 24 hrs | GLY conversion rate (%) | 94.8 | 91.4 | 100.0 | 96.7 | 92.2 | 96.7 | 78.9 | 84.2 | 72.4 |
| | ACR yield (%) | 65.9 | 57.3 | 65.6 | 62.2 | 59.6 | 63.1 | 41.3 | 42.3 | 28.9 |
| From 35.5 to 36 hrs | GLY conversion rate (%) | 90.5 | 90.1 | 92.0 | 87.8 | 81.1 | 87.7 | 72.2 | 69.1 | 63.1 |
| | ACR yield (%) | 58.8 | 47.9 | 55.4 | 46.0 | 49.5 | 31.0 | 33.6 | 26.7 | |
| From 47.5 to 48 hrs | GLY conversion rate (%) | 80.8 | 86.3 | 85.9 | 71.0 | 70.1 | 80.3 | 64.3 | 65.4 | 57.7 |
| | ACR yield (%) | 51.8 | 41.8 | 41.0 | 41.5 | 37.8 | 42.9 | 27.2 | 27.5 | 23.3 |
| Amounts of carbonaceous substances (% by mass) | | — | 11 | 9 | — | 11 | 9 | — | 11 | — |

GLY: glycerin
ACR: acrolein

TABLE 4

| | | Experimental Examples | | |
|---|---|---|---|---|
| | | 29 | 30 | 31 |
| Catalysts | | Catalyst A | Catalyst B | |
| Partial pressure of GLY gas (kPa) | | 27.7 | 4.7 | 16.2 |
| Partial pressure of water vapor (kPa) | | 35.4 | 23.0 | 21.2 |
| Partial pressure at inlet of reactor (kPa) | | 63.1 | 27.7 | 37.4 |
| Partial pressure of water vapor/ partial pressure of GLY (kPa/kpa) | | 1.28 | 4.9 | 1.3 |
| GHSV of raw material gas (hr$^{-1}$) | | 403 | 952 | 382 |
| GHSV of GLY (hr$^{-1}$) | | 177 | 169 | |
| From 0.5 to 1.0 hr | GLY conversion rate (%) | 100.0 | 100.0 | 100.0 |
| | ACR yield (%) | 59.8 | 56.2 | 60.1 |
| From 5.5 to 6.0 hrs | GLY conversion rate (%) | 100.0 | — | — |
| | ACR yield (%) | 64.5 | — | — |
| From 11.5 to 12.0 hrs | GLY conversion rate (%) | — | 100.0 | 95.6 |
| | ACR yield (%) | — | 69.9 | 63.3 |
| From 23.5 to 24.0 hrs | GLY conversion rate (%) | — | 99.5 | 80.4 |
| | ACR yield (%) | — | 65.7 | 42.5 |
| From 35.5 to 36.0 hrs | GLY conversion rate (%) | — | 96.8 | 75.9 |
| | ACR yield (%) | — | 63.8 | 39.7 |
| From 47.5 to 48.0 hrs | GLY conversion rate (%) | — | 88.9 | 65.2 |
| | ACR yield (%) | — | 56.1 | 28.1 |
| Amount of carbonaceous substances (% by mass) | | 12 | 8 | — |

GLY: glycerin
ACR: acrolein

In comparison of Experimental Examples 1 to 3, 4 to 6, or 7 to 9 in Table 1, it is found that regardless of the partial pressure of water vapor supplied together, the yield of acrolein was high particularly when the partial pressure of glycerin gas was in a range of from 4 to 9 kPa. Table 1 also shows that the amount of carbonaceous substances accumulated was smaller when the partial pressure of glycerin gas was more lowered, regardless of the partial pressure of water vapor. Further, in comparison of Experimental Examples 8 to 9 and 10 to 11, it is found that although GHSV of glycerin gas was increased two times, the yield of acrolein was not different so much. On the other hand, in Experimental Example 19 in which the partial pressure of glycerin gas was 33 kPa, which was higher than 30 kPa, the yield of acrolein was as high as 70 mol % in the initial period of the acrolein production; however, it is found that the yield of acrolein was remarkably decreased with time and the amount of carbonaceous substances accumulated on the catalyst was increased as much as 23% by mass.

In comparison of Experimental Examples 13 to 18 in Table 2 with the results of feeding water vapor together, it is found that the partial pressure of water vapor at the inlet of the reactor was 0 kPa in the Experimental Examples 13 to 18, the results of which were, however, equal to or better than those as shown in Table 1 to be compared. That is, Tables 1 and 2 show that the amount of carbonaceous substances accumulated was correlated with the partial pressure of glycerin gas and the partial pressure of glycerin gas was the main factor of the yield of acrolein and the accumulation of carbonaceous substances.

In Experimental Examples 20 to 28 in Table 3 using the catalyst B, in the same manner as in the results of the catalyst A shown in Table 1, it was also found that the yield of acrolein was more excellent and the amount of carbonaceous substances accumulated was smaller as the partial pressure of glycerin gas was more lowered. For example, a comparison of Experimental Examples 22 and 24, shows that the better results were obtained as the partial pressure of glycerin gas was lower. In Comparison Example 1 in which although the GHSV of glycerin gas was 338 hr$^{-1}$, the partial pressure of glycerin gas was as high as 33 kPa, the conversion rate of glycerin was not changed; however, the yield of acrolein was rapidly decreased, and therefore, it was found that the life of the catalyst was short.

Further, in comparison of Experimental Examples 12 and 29 in which the partial pressure of glycerin gas was substantially the same but the concentration of glycerin in the raw material gas was remarkably different as being Experimental Example 12:Experimental Example 29=27 mol %:44 mol %, the yield of acrolein was not different so much in both the Experimental Examples. This was also the same in comparison of the results of Experimental Examples 27 and 31. From these results, it is found that the partial pressure of glycerin gas was important, but not the total pressure or gas concentration of a raw material gas.

Further, since it is confirmed that the same effect by the partial pressure of glycerin gas as described above was attained in the case of using the catalyst A composed of weakly acidic aluminum phosphate and the catalyst B composed of strongly acidic HZSM5, solid acid catalysts can be used regardless of their acid strengths.

Accordingly, it is found that if the partial pressure of glycerin gas in a raw material gas is adjusted to be 30 kPa or lower and a solid acid catalyst is used, the yield of acrolein can be made excellent and the life of the catalyst can be prolonged without using an excess amount of water vapor unlike the disclosures of the prior art documents. That is, acrolein can be produced under the conditions of saving energy for generating water vapor, decreasing the amount of wastewater to be generated, and reducing a load on environments.

Catalysts C to E were prepared according to the following Catalyst Preparation Examples C, D, or E. Using the catalyst C, D, or E, acrolein was produced according to the following Experimental Examples 32 to 44.

Catalyst Preparation Example C

The catalyst C, which was H-type MFI, was obtained in the same manner as described in Catalyst Preparation Example B.

Catalyst Preparation Example D

A commercially available granular active alumina ("ALUMINIUMOXIDE90 Active Acidic, 0.063-0.200 mm, Activity STAGE I", available from Merk & Co., Inc.; Production No. 101078) was filled in a cylinder made of poly(vinyl chloride) and having an inner diameter of 3 cm and a height of 5 mm, followed by pressure forming. The resultant formed product was crushed and classified to obtain the catalyst D having sizes of from 0.7 to 1.4 mm.

Catalyst Preparation Example E

A mixed solution was prepared by mixing 350 g of ion-exchanged water and 40 g of $SiO_2$ powder, followed by stirring, and the mixed solution was heated to 80° C. Then, 7.1573 g of $ZrO(NO_3)_2 \cdot 2H_2O$ dissolved in a small amount of water and 6.1507 g of an aqueous solution containing 85% by mass of orthophosphoric acid were added to the mixed solution.

The mixed solution was heated at 80° C. under stirring until the solution became a paste form. The resultant paste-form material was dried at 100° C. and then calcinated under air atmosphere at 600° C. for 5 hours to obtain a solid substance. The solid substance was crushed and classified to obtain the catalyst E having sizes of from 0.7 to 1.4 mm.

Experimental Example 32

A stainless steel reaction tube (having an inner diameter of 10 mm and a length of 500 mm) filled with 15 mL of the catalyst C was prepared as a fixed bed reactor. This reactor was immersed in a molten salt bath at 360° C., and a raw material gas (raw material gas composition: 27 mol % glycerin, 34 mol % water, and 39 mol % nitrogen) was then fed into the reactor at a flow rate (GHSV) of 632 $hr^{-1}$. Under these conditions, the feed amount of glycerin gas per 1 L of the catalyst was 701 g/hr and the contact time was 5.7 seconds. As a result of the analysis, by GC, of the flowing-out material for a period extending from 30 to 60 minutes after the start of the feeding of the raw material gas into the reactor and the flowing-out material for a period extending from 150 to 180 minutes after the start of the feeding of the raw material gas into the reactor, glycerin, acrolein, and 1-hydroxyacetone were detected. The results of Experimental Example 32 are shown in Table 5 below.

Experimental Example 33

Acrolein was produced in the same manner as described in Experimental Example 32, except that the catalyst amount of 15 mL was changed to 7.5 mL. The feed amount of glycerin gas per 1 L of the catalyst was 1,400 g/hr and the contact time was 2.8 seconds. The results are shown in Table 5 below.

Experimental Example 34

Acrolein was produced in the same manner as described in Experimental Example 32, except that the molten salt bath temperature of 360° C. was changed to 390° C. The results are shown in Table 5 below.

Experimental Example 35

Acrolein was produced in the same manner as described in Experimental Example 32, except that the molten salt bath temperature of 360° C. was changed to 390° C. and the catalyst amount of 15 mL was changed to 4 mL. The feed amount of glycerin gas per 1 L of the catalyst was 2,625 g/hr and the contact time was 1.5 seconds. The results are shown in following Table 5 below.

Experimental Example 36

Acrolein was produced in the same manner as described in Experimental Example 32, except that the molten salt bath temperature of 360° C. was changed to 420° C. and the catalyst amount of 15 mL was changed to 4 mL. The feed amount of glycerin gas per 1 L of the catalyst was 2,625 g/hr and the contact time was 1.5 seconds. The results are shown in Table 5 below.

Experimental Example 37

Acrolein was produced in the same manner as described in Experimental Example 32, except that the molten salt bath temperature of 360° C. was changed to 420° C. and the catalyst amount of 15 mL was changed to 2 mL. The feed amount of glycerin gas per 1 L of the catalyst was 5,250 g/hr and the contact time was 0.76 seconds. The results are shown in Table 5 below.

Experimental Example 38

Acrolein was produced in the same manner as described in Experimental Example 32, except that the molten salt bath temperature of 360° C. was changed to 450° C. and the catalyst amount of 15 mL was changed to 2 mL. The feed amount of glycerin gas per 1 L of the catalyst was 5,250 g/hr and the contact time was 0.76 seconds. The results are shown in Table 5 below.

Experimental Example 39

Acrolein was produced in the same manner as described in Experimental Example 32, except that the molten salt bath temperature of 360° C. was changed to 450° C. and the catalyst amount of 15 mL was changed to 1 mL. The feed amount of glycerin gas per 1 L of the catalyst was 10,500 g/hr and the contact time was 0.38 seconds. The results are shown in Table 5 below.

Experimental Example 40

Acrolein was produced in the same manner as described in Experimental Example 32, except that the catalyst C was changed to the catalyst D. The results are shown in Table 5 below.

Experimental Example 41

Acrolein was produced in the same manner as described in Experimental Example 32, except that the catalyst C was changed to the catalyst E. The results are shown in Table 5 below.

Experimental Example 42

Acrolein was produced in the same manner as described in Experimental Example 32, except that the molten salt bath temperature was set to be 300° C. The results are shown in Table 5 below.

Experimental Example 43

Acrolein was produced in the same manner as described in Experimental Example 39, except that the molten salt bath temperature was set to be 480° C. The results are shown in Table 5 below.

Experimental Example 44

Acrolein was produced in the same manner as described in Experimental Example 32, except that the molten salt bath temperature was set to be 390° C. and a raw material gas was used, of which composition was 6.2 mol % glycerin, 7.9 mol % water, and 85.9 mol % nitrogen. The results are shown in Table 5 below.

TABLE 5

| | Reaction temperature (° C.) | GLY feed amount (g/hr) | Contact Time (sec.) | From 30 to 60 min. | | From 150 to 180 min. | |
|---|---|---|---|---|---|---|---|
| | | | | GLY conversion rate (%) | ACR yield (%) | GLY conversion rate (%) | ACR yield (%) |
| Experimental Example 32 | 360 | 701 | 5.7 | 99.9 | 62.3 | 99.8 | 66.5 |
| Experimental Example 33 | 360 | 1,400 | 2.8 | 100.0 | 59.8 | 100.0 | 70.4 |
| Experimental Example 34 | 390 | 701 | 5.7 | 100.0 | 35.4 | 100.0 | 54.8 |
| Experimental Example 35 | 390 | 2,625 | 1.5 | 100.0 | 66.2 | 100.0 | 66.3 |
| Experimental Example 36 | 420 | 2,625 | 1.5 | 100.0 | 53.2 | 100.0 | 53.3 |
| Experimental Example 37 | 420 | 5,250 | 0.76 | 100.0 | 54.8 | 99.8 | 52.3 |
| Experimental Example 38 | 450 | 5,250 | 0.76 | 100.0 | 56.1 | 100.0 | 45.1 |
| Experimental Example 39 | 450 | 10,500 | 0.38 | 100.0 | 59.0 | 99.6 | 35.7 |
| Experimental Example 40 | 360 | 701 | 5.7 | 100.0 | 30.2 | 99.9 | 45.0 |
| Experimental Example 41 | 360 | 701 | 5.7 | 98.2 | 62.5 | 91.9 | 55.5 |
| Experimental Example 42 | 300 | 701 | 5.7 | 93.9 | 61.5 | 55.8 | 22.8 |
| Experimental Example 43 | 480 | 10,500 | 0.38 | 100.0 | 0.0 | 100.0 | 3.5 |
| Experimental Example 44 | 390 | 161 | 5.7 | 100.0 | 11.1 | 100.0 | 25.3 |

GLY feed amount: feed amount of glycerin gas per 1 L of catalyst
GLY: glycerin
ACR: acrolein The confirmation of Table 5 shows the following. In Experimental Example 42 in which the reaction temperature was set to be 300° C., the activity of the catalyst was rapidly decreased. In Experimental Example 43 in which the reaction temperature was set to be 480° C., acrolein was not able to be sufficiently obtained. Further, in Experimental Example 44 in which the reaction temperature was increased, since the feed amount of glycerin gas per 1 L of the catalyst was small, the yield of acrolein became low. On the other hand, when the feed amount of glycerin gas per 1 L of the catalyst was set to be from 300 to 15,000 g/hr and the reaction temperature was set to be from 350° C. to 460° C., the yield of acrolein was excellent.

According to the following Catalyst Preparation Example F, an H-type MFI formed product containing Al as T atom was produced as a catalyst F. Using this catalyst F, acrolein was produced according to the following Experimental Examples 45 to 47.

Catalyst Preparation Example F

First, 1.40 g of NaOH was dissolved in 15.00 g of distilled water, and 0.47 g of NaAlO$_2$ (available from Asada Chemical Industry Co., Ltd.; purity: 86.8% by mass) was successively dissolved in the distilled water, and 10.15 g of an aqueous solution containing 40% by mass of tetra-n-propylammonium hydroxide was further added to the distilled water. Then, distilled water was added to the resultant solution to produce an impregnating solution having a total amount of 30 mL. Then, silica beads ("CARiACT Q-50", available from Fuji Silysia Chemical Ltd.; from 10 to 20 meshes; average fine pore diameter: 50 nm) were used as a silica formed product, and 30 g of the silica beads dried at 120° C. for 1 day were impregnated with the impregnating solution for 1 hour. Then, the silica beads were dried on an evaporating dish placed on a hot water bath at 100° C. and further dried at 80° C. under a nitrogen stream for 7 hours, thereby allowing Na, Al, and a crystallization agent necessary for crystallization to be supported on the silica beads to obtain a crystalline methanosilicate precursor. The resultant precursor was placed in the hollow position of a jacket-bearing crucible made of polytetrafluoroethylene and having a capacity of 100 mL, and 1.00 g of distilled water was put in the bottom position of the crucible. This crucible was allowed to stand still in an electric furnace at 180° C. for 8 hours to crystallize the precursor. The solid substance obtained by the crystallization was immersed in 300 g of an aqueous solution containing 1 mol/L of ammonium nitrate at 60° C., and the mixture was stirred for 1 hour, after which the supernatant solution was discarded. This operation was repeated more than once. Then, the solid substance was washed with water. The solid substance was calcinated in an air stream at 540° C. for 3.5 hours. The catalyst F, which was H-type MFI, was obtained by this calcination.

Experimental Example 45

A stainless steel reaction tube (having an inner diameter of 10 mm and a length of 500 mm) filled with 15 mL of the catalyst F was prepared as a fixed bed reactor. An evaporator filled with glass beads each having an outer diameter of 3 mm was provided on the inlet side of the reactor, and the temperature control of the evaporator was carried out while the temperature was monitored by a thermocouple inserted into the evaporator. The reaction pressure was controlled using a vacuum pump and a vacuum controller while the pressure was monitored by a pressure meter provided at the inlet of the reactor. Further, a cooling apparatus was provided at the outlet of the reactor.

The reactor was immersed in a molten salt bath at 360° C. The temperature of the evaporator was set to be 200° C. and the inner pressure of the reactor was set to be 62 kPa, at which the reactor was kept for 30 minutes, and then, an aqueous solution containing 80% by mass of glycerin was fed to the evaporator by a solution sending pump. In addition, the temperature of the evaporator was assumed to be 192° C. at the time of evaporating the aqueous solution containing 80% by mass glycerin.

A raw material gas (raw material gas composition: 44 mol % glycerin and 56 mol % water) generated by the above evaporator was fed into the reactor at a flow rate of 490 hr$^{-1}$ in terms of SV value. The total amount of a gas flowing out for a period extending from 0.5 to 1 hour after the start of the feeding and a gas flowing out for a period extending from 2.5 to 3 hours after the start of the feeding was collected in a receiver cooled in a dry ice and methanol bath. As a result of the analysis, by GC, of the collected flowing-out material, glycerin, acrolein, and 1-hydroxyacetone were detected. The results are shown in Table 6 below.

Experimental Example 46

Acrolein was produced in the same manner as described in Experimental Example 45, except that the temperature of the evaporator was set to be 250° C.; the inner pressure of the reactor, 27 kPa; the raw material gas concentration, 100 mol % glycerin; and the SV value, 180 hr$^{-1}$. In this production, the temperature of the evaporator at the time of evaporating the glycerin solution was estimated to be 244° C. The results are shown in Table 6 below.

Experimental Example 47

Acrolein was produced under the production conditions which can be compared with those of Experimental Examples 45 and 46. In Experimental Example 47, a noncondensable gas was used as a dilution gas, and acrolein was produced under the condition of atmospheric pressure as follows.

A stainless steel reaction tube (having an inner diameter of 10 mm and a length of 500 mm) filled with 15 mL of the catalyst F was prepared as a fixed bed reactor. The reactor was immersed in a molten salt bath at 360° C. The temperature of the evaporator was set to be 310° C. and nitrogen was fed into the reactor at a flow rate of 62 mL/min for 30 minutes, and then, glycerin was fed to the evaporator by a solution sending pump. In this production, the temperature of the evaporator at the time of evaporating the glycerin solution was assumed to be 290° C. or higher.

A raw material gas containing glycerin gas generated by the above evaporator and nitrogen (raw material gas composition: 27 mol % glycerin and 73 mol % nitrogen) was fed into the reactor at a flow rate (GHSV) of 650 hr$^{-1}$. Under these production conditions, the partial pressure of nitrogen was subtracted from the total pressure of the raw material gas to give the pressure of the raw material gas in Experimental Example 46. A gas flowing out for a period extending from 0.5 to 1 hour after the start of the feeding of the raw material gas and a gas flowing out for a period extending from 2.5 to 3 hours after the start of the feeding of the raw material gas were separately absorbed in water. Using a part of this water as a sample, analysis by GC was carried out. The results are shown in Table 6 below.

TABLE 6

| No. | Passing time (min.) | Raw material gas composition (vol. %) | | | Pressure (kPa) Raw material gas | GLY gas | GLY conversion rate (mol %) | ACR yield (mol %) |
|---|---|---|---|---|---|---|---|---|
| | | GLY | H$_2$O | N$_2$ | | | | |
| Experimental Example 45 | from 30 to 60 | 44 | 56 | 0 | 62 | 27 | 100 | 66.3 |
| | from 150 to 180 | 44 | 56 | 0 | 62 | 27 | 100 | 66.3 |
| Experimental Example 46 | from 30 to 60 | 100 | 0 | 0 | 27 | 27 | 100 | 63.5 |
| | from 150 to 180 | 100 | 0 | 0 | 27 | 27 | 100 | 68.4 |
| Experimental Example 47 | from 30 to 60 | 27 | 0 | 73 | 101 | 27 | 98.0 | 52.4 |

GLY: glycerin,
ACR: acrolein

As shown in Table 6, it has been known that even if the total pressure of the reaction system is different in the gas-phase reaction, when the partial pressure of a raw material is constant, the yield usually becomes substantially the same; however, Experimental Examples 45 and 46 carried out under the reduced pressure condition are excellent in yield.

As shown in Table 6, in the gas-phase dehydration of glycerin, it is found that if the pressure of the reaction system was controlled to be reduced pressure, the yield of acrolein can be made high when the concentration of glycerin gas was high and no water was present. That is, when the pressure at the inlet of a reactor was not lower than 1 kPa and not higher than 90 kPa, even if no water was contained in the raw material gas, acrolein can be produced at a high yield and at a low cost.

According to the following Catalyst Preparation Examples G and H, catalysts G and H were produced. Using the catalyst G or H, acrolein was produced according to the following Experimental Examples 48 to 53.

Catalyst Preparation Example G

The catalyst G, which was an H-type MFI, was produced in the same manner as described in Catalyst Preparation Example B.

Catalyst Preparation Example H

A commercially available granular active alumina ("ALUMINIUMOXIDE90 ACTIVE ACIDIC, 0.063-0.200 mm", available from Merk & Co., Inc.; Production No. 101078) was calcinated under air atmosphere at 500° C. for 2 hours. The resultant calcinated material was filled in a cylinder made of poly(vinyl chloride) and having an inner diameter of 3 cm and a height of 5 mm, followed by pressure forming. The resultant formed product was crushed and classified to obtain the catalyst H having sizes of from 0.7 to 1.4 mm.

Experimental Example 48

A stainless steel reaction tube (having an inner diameter 10 mm and a length of 500 mm) filled with 15 mL of the catalyst G was prepared as a fixed bed reactor. This reactor was immersed in a molten salt bath at 360° C., and a raw material gas was then fed into the reactor. As the raw material gas, a mixture of nitrogen at a flow rate of 61.5 mL/min and glycerin at a flow rate of 13.15 g/hr was used, and as the glycerin-containing composition, a composition containing glycerin: palmitic acid:water=80% by mass:0.1% by mass:19.9% by mass was used. As a result of the analysis of the flowing-out material for a period extending from 0 to 30 minutes after the start of the feeding of the raw material gas into the reactor, the flowing-out material for a period extending from 30 to 60 minutes after the start of the feeding of the raw material gas into the reactor, and the flowing-out material for a period extending from 150 to 180 minutes after the start of the feeding of the raw material gas into the reactor, glycerin, acrolein, and 1-hydroxyacetone were detected. The results are shown in Table 7 below.

Experimental Example 49

Acrolein was produced in the same manner as described in Experimental Example 48, except that the catalyst G was changed to the catalyst H. The results are shown in Table 7 below.

Experimental Example 50

Acrolein was produced in the same manner as described in Experimental Example 48, except that the glycerin-containing composition containing glycerin: palmitic acid:water=80% by mass:0.1% by mass:19.9% by mass was changed to a glycerin-containing composition containing glycerin: palmitic acid:water=80% by mass:1.0% by mass:19.0% by mass. The results are shown in Table 7 below.

Experimental Example 51

Acrolein was produced in the same manner as described in Experimental Example 48, except that palmitic acid was changed to methyl palmitate. The results are shown in Table 7 below.

Experimental Example 52

Acrolein was produced in the same manner as described in Experimental Example 48, except that a composition containing glycerin:water=80% by mass:20% by mass was used as the glycerin-containing composition. The results are shown in Table 7 below.

Experimental Example 53

Acrolein was produced in the same manner as described in Experimental Example 49, except that a composition containing glycerin:water=80% by mass:20% by mass was used as the glycerin-containing composition. The results are shown in Table 7 below.

TABLE 7

| | Catalyst | Fatty acids Kind | Content based on glycerin (% by mass) | Acrolein yield (%) From 0 to 30 min. | From 30 to 60 min. | From 150 to 180 min. |
|---|---|---|---|---|---|---|
| Experimental Example 48 | H-type MFI | Palmitic acid | 0.125 | 24.6 | 64.1 | 66.7 |
| Experimental Example 49 | Activated alumina | Palmitic acid | 0.125 | 17.2 | 40.1 | 42.2 |
| Experimental Example 50 | H-type MFI | Palmitic acid | 1.25 | 25.7 | 66 | 66.3 |
| Experimental Example 51 | H-type MFI | Methyl palmitate | 0.125 | 23.9 | 64.8 | 66.4 |
| Experimental Example 52 | H-type MFI | — | 0 | 22.5 | 62.3 | 66.5 |
| Experimental Example 53 | Activated alumina | — | 0 | 13.5 | 39.4 | 42.1 |

Glycerin conversion rate: All 100%

In Experimental Examples 52 and 53, it is found that the yield of acrolein was extremely low for a period extending from 0 to 30 minutes, which was the initial period of dehydration, and this was the induction period. On the other hand, it is found that in Experimental Examples 48 to 50 using the glycerin-containing composition containing palmitic acid and Experimental Example 51 using the glycerin-containing composition containing methyl palmitate, the yield of acrolein was improved for a period extending from 0 to 30 minutes and for a period extending from 30 to 60 minutes, and the induction period was made short. Accordingly, it is found that if acrolein is produced using a glycerin-containing composition containing fatty acids as one kind of component, the yield of acrolein can be kept stable immediately after the start of the feeding of the raw material gas to the reactor and acrolein can be produced at a high yield.

According to the following Catalyst Preparation Examples I and J, catalysts I and J were prepared. Using the catalyst I or J, acrolein was produced according to the following Experimental Examples 54 to 71.

Catalyst Preparation Example I

The catalyst I, which was H-type MFI, was obtained in the same manner as described in Catalyst Preparation Example B.

Catalyst Production Example J

A commercially available granular active alumina ("ALU-MINIUMOXIDE90 Active acidic, 0.063-0.200 mm, Activity STAGE I", available from Merk & Co., Inc.; Production No. 101078) was calcinated under air atmosphere at 500° C. for 2 hours, and then filled in a cylinder made of poly(vinyl chloride) and having an inner diameter of 3 cm and a height of 5 mm, followed by pressure forming. The resultant formed product was crushed and classified to obtain the catalyst J having sizes of from 0.7 to 1.4 mm.

Experimental Example 54

Acrolein Production Step (1)-1

A stainless steel reaction tube (having an inner diameter 10 mm and a length of 500 mm) filled with 15 mL of the catalyst I was prepared as a fixed bed reactor. This reactor was immersed in a molten salt bath at 360° C., and nitrogen was fed into the reactor at 62 N mL/min for 30 minutes and a raw material gas (raw material gas composition: 27 mol % glycerin, 34 mol % water, and 39 mol % nitrogen) was then fed into the reactor at a flow rate (GHSV) of 632 hr$^{-1}$. While the molten salt bath temperature was kept at 360° C., the raw material gas was fed into the reactor for 12 hours and only the passing of glycerin and water was then stopped but nitrogen was fed into the reactor for 30 minutes to discharge an organic gas remaining in the reactor. As a result of the analysis of flowing-out material for a period extending from 0.5 to 1 hour after the start of the feeding of the raw material gas into the reactor and the flowing-out material for a period extending from 11.5 to 12.0 hours after the start of the feeding of the raw material gas into the reactor, glycerin, acrolein, and 1-hydroxyacetone were detected. The feed amount of glycerin per 1 L of the catalyst I was 701 g/hr and the contact time was 5.7 seconds.

Reactivation Step (2)

After the acrolein production step (1), the reactor filled with the catalyst I was kept in the state of immersion in the molten salt bath. The molten salt bath temperature was changed to 450° C., and while the temperature was kept in this state, air was fed into the reactor at 62 N mL/min. The reactivation treatment of the catalyst was carried out in such a manner.

Acrolein Production Step (1)-2

Using the reactor after the reactivation step (2), acrolein was produced in the same manner as described in the acrolein production step (1)-1.

In Experimental Example 54, the temperature at the time of finishing in the acrolein production step (1)-1 was 360° C. and the temperature at the time of starting in the reactivation step (2) was 450° C. Tm(2) was 450° C.; the temperature at the time of finishing in the reactivation step (2) was 450° C.; and the temperature at the time of starting in the acrolein production step (1)-2 was 360° C. The results are shown in Table 8 below.

Experimental Example 55

Acrolein was produced in the same manner as described in Experimental Example 54, except that the molten salt bath temperature in the reactivation step (2) was changed to 360° C. The temperature at the time of finishing in the step (1)-1 was 360° C.; the temperature at the time of starting in the step (2) was 360° C.; Tm(2) was 360° C.; the temperature at the time of finishing in the step (2) was 360° C.; and the temperature at the time of starting in the step (1)-2 was 360° C. The results are shown in Table 8 below.

Experimental Example 56

Acrolein was produced in the same manner as described in Experimental Example 54, except that the catalyst I was changed to the catalyst J and the molten salt bath temperature in the reactivation step (2) was changed to 360° C. The temperature at the time of finishing in the step (1)-1 was 360° C.; the temperature at the time of starting in the step (2) was 360° C.; Tm(2) was 360° C.; the temperature at the time of finishing in the step (2) was 360° C.; and the temperature at the time of starting in the step (1)-2 was 360° C. The results are shown in Table 8 below.

Experimental Example 57

Acrolein was produced in the same manner as described in Experimental Example 54, except that the temperature at the time of starting in the reactivation step (2) was set to be 280° C. and increased to 360° C. at a temperature increasing speed of +10° C./hr. The temperature at the time of finishing in the step (1)-1 was 360° C.; the temperature at the time of starting in the step (2) was 280° C.; Tm(2) was 360° C.; the temperature at the time of finishing in the step (2) was 360° C.; and the temperature at the time of starting in the step (1)-2 was 360° C. The results are shown in Table 8 below.

Experimental Example 58

Acrolein was produced in the same manner as described in Experimental Example 54, except that the temperature in the reactivation step (2) was set to be 250° C. The temperature at the time of finishing in the step (1)-1 was 360° C.; the temperature at the time of starting in the step (2) was 250° C.; Tm(2) was 250° C.; the temperature at the time of finishing in the step (2) was 250° C.; and the temperature at the time of starting in the step (1)-2 was 360° C. The results are shown in Table 8 below.

Experimental Example 59

Acrolein was produced in the same manner as described in Experimental Example 54, except that the catalyst I was changed to the catalyst J and the temperature in the reactivation step (2) was set to be 250° C. The temperature at the time of finishing in the step (1)-1 was 360° C.; the temperature at the time of starting in the step (2) was 250° C.; Tm(2) was 250° C.; the temperature at the time of finishing in the step (2) was 250° C.; and the temperature at the time of starting in the step (1)-2 was 360° C. The results are shown in Table 8 below.

TABLE 8

| | | Experimental Example 54 | Experimental Example 55 | Experimental Example 56 | Experimental Example 57 | Experimental Example 58 | Experimental Example 59 |
|---|---|---|---|---|---|---|---|
| | Catalyst | Catalyst I | Catalyst I | Catalyst J | Catalyst I | Catalyst I | Catalyst J |
| | Reaction temperature | 360 | 360 | 360 | 360 | 360 | 360 |
| | GLY feed amount (g/hr) | 701 | 701 | 701 | 701 | 701 | 701 |
| | Contact time | 5.7 | 5.7 | 5.7 | 5.7 | 5.7 | 5.7 |
| From 0.5 to 1.0 hr | GLY conversion rate (%) | 100 | 100 | 100 | 99.9 | 100 | 100 |
| | ACR yield (%) | 62.8 | 64.1 | 28.2 | 62.5 | 63.1 | 29.4 |
| From 11.5 to 12.0 hrs | GLY conversion rate (%) | 93.5 | 95.1 | 100 | 93.7 | 94.2 | 100 |
| | ACR yield (%) | 52.6 | 54.6 | 45.6 | 52.4 | 51.8 | 44.8 |
| | DT (12) | 90 | 0 | 0 | 80 | 110 | 110 |
| | Tm (2) | 450 | 360 | 360 | 360 | 250 | 250 |
| | DT (21) | 90 | 0 | 0 | 0 | 110 | 110 |
| From 0.5 to 1.0 hr | GLY conversion rate (%) | 100 | 100 | 100 | 100 | 93.1 | 100 |
| | ACR yield (%) | 63.8 | 63.1 | 29.3 | 64 | 50.8 | 45.2 |
| From 11.5 to 12.0 hrs | GLY conversion rate (%) | 94.5 | 88.8 | 100 | 93.9 | 72.9 | 94.4 |
| | ACR yield (%) | 53.6 | 49.1 | 45.6 | 53.9 | 42.3 | 43.1 |

GLY feed amount: feed amount of glycerin gas per 1 L of catalyst
GLY: glycerin
ACR: acrolein In comparison of Experimental Examples 54 to 56 and 58 to 59, it is found that if the reactivation temperature was 300° C. or lower, the catalyst was not able to be reactivated. Further, from the results of Experimental Example 57, it is found that if Tm(2) was 300° C. or higher, the catalyst was able to be reactivated, even when the reactivation starting temperature was 300° C. or lower. Further, it is found that if DT(12) or DT(21) was small, the acrolein production step (1) and the reactivation step (2) was able to be switched within a short time.

Experimental Example 60

Acrolein Production Step (1)-1

A stainless steel reaction tube (having an inner diameter of 10 mm and a length of 500 mm) filled with 15 mL of the catalyst I was prepared as a fixed bed reactor. This reactor was immersed in a molten salt bath at 330° C., and nitrogen was fed into the reactor at 62 N mL/min for 30 minutes and a raw material gas (raw material gas composition: 27 mol % glycerin, 34 mol % water, and 39 mol % nitrogen) was fed into the reactor at a flow rate (GHSV) of 632 hr$^{-1}$. While the molten salt bath temperature was kept at 330° C., the raw material gas was fed into the reactor for 12 hours and only the feeding of glycerin and water was stopped but nitrogen was fed into the reactor for 30 minutes to discharge an organic gas remaining in the reactor. As a result of the analysis of the flowing-out material for a period extending from 0.5 to 1 hour after the start of the feeding of the raw material gas into the reactor and the flowing-out material for a period extending from 2.5 to 3.0 hours after the start of the feeding of the raw material gas into the reactor, glycerin, acrolein, and 1-hydroxyacetone were detected. The feed amount of glycerin per 1 L of the catalyst I was 701 g/hr and the contact time was 5.7 seconds.

Experimental Example 61

Experimental Example 61 was carried out in the same manner as described in Experimental Example 60, except the molten salt bath temperature was changed to 300° C. The results are shown in Table 9 below.

Experimental Example 62

Experimental Example 62 was carried out in the same manner as described in Experimental Example 60, except the molten salt bath temperature was changed to 360° C. The results are shown in Table 9 below.

TABLE 9

| | Reaction temperature (° C.) | GLY feed amount (g/hr) | Contact time (sec.) | From 0.5 to 1.0 hr | | From 2.5 to 3.0 hrs | |
| --- | --- | --- | --- | --- | --- | --- | --- |
| | | | | GLY conversion rate (%) | ACR yield (%) | GLY conversion rate (%) | ACR yield (%) |
| Experimental Example 61 | 300 | 701 | 5.7 | 93.9 | 61.5 | 55.8 | 22.8 |
| Experimental Example 60 | 330 | 701 | 5.7 | 100.0 | 64.3 | 100.0 | 67.1 |
| Experimental Example 62 | 360 | 701 | 5.7 | 100.0 | 62.3 | 100.0 | 66.5 |

GLY feed amount: feed amount of glycerin gas per 1 L of catalyst
GLY: glycerin
ACR: acrolein In comparison of Experimental Example 61 and Experimental Examples 60 and 62 as shown in Table 9, it is found that if the reaction temperature (the molten salt bath temperature) was higher than 300° C., the yield of acrolein was excellent.

Experimental Example 63

Acrolein was produced in the same manner as described in Experimental Example 62, except that the catalyst amount was changed from 15 mL to 7.5 mL. The feed amount of glycerin per 1 L of the catalyst was 1,400 g/hr and the contact time was 2.8 seconds. The results are shown in Table 10 below.

Experimental Example 64

Acrolein was produced in the same manner as described in Experimental Example 62, except that the molten salt bath temperature was changed from 360° C. to 390° C. The results are shown in Table 10 below.

Experimental Example 65

Acrolein was produced in the same manner as described in Experimental Example 62, except that the molten salt bath temperature was changed from 360° C. to 390° C. and the catalyst amount was changed from 15 mL to 4 mL. The feed amount of glycerin per 1 L of the catalyst was 2,625 g/hr and the contact time was 1.5 seconds. The results are shown in Table 10 below.

Experimental Example 66

Acrolein was produced in the same manner as described in Experimental Example 62, except that the molten salt bath temperature was changed from 360° C. to 420° C. and the catalyst amount was changed from 15 mL to 4 mL. The feed amount of glycerin per 1 L of the catalyst was 2,625 g/hr and the contact time was 1.5 seconds. The results are shown in Table 10 below.

Experimental Example 67

Acrolein was produced in the same manner as described in Experimental Example 62, except that the molten salt bath temperature was changed from 360° C. to 420° C. and the catalyst amount was changed from 15 mL to 2 mL. The feed amount of glycerin per 1 L of the catalyst was 5,250 g/hr and the contact time was 0.76 seconds. The results are shown in Table 10 below.

Experimental Example 68

Acrolein was produced in the same manner as described in Experimental Example 62, except that the molten salt bath temperature was changed from 360° C. to 450° C. and the catalyst amount was changed from 15 mL to 2 mL. The feed amount of glycerin per 1 L of the catalyst was 5,250 g/hr and the contact time was 0.76 seconds. The results are shown in Table 10 below.

Experimental Example 69

Acrolein was produced in the same manner as described in Experimental Example 62, except that the molten salt bath temperature was changed from 360° C. to 450° C. and the catalyst amount was changed from 15 mL to 1 mL. The feed amount of glycerin per 1 L of the catalyst was 10,500 g/hr and the contact time was 0.38 seconds. The results are shown in Table 10 below.

Experimental Example 70

Acrolein was produced in the same manner as described in Experimental Example 69, except that the molten salt bath temperature was set to be 480° C. The results are shown in Table 10 below.

Experimental Example 71

Acrolein was produced in the same manner as described in Experimental Example 62, except that the molten salt bath temperature was set to be 390° C. and a composition containing 6.2 mol % glycerin, 7.9 mol % water, and 85.9 mol % nitrogen was used as the raw material gas. The results are shown in Table 10 below.

TABLE 10

|  | Reaction temperature (°C.) | GLY feed amount (g/hr) | Contact time (second) | From 0.5 to 1.0 hr | | From 2.5 to 3.0 hrs | |
|---|---|---|---|---|---|---|---|
|  |  |  |  | GLY conversion rate (%) | ACR yield (%) | GLY conversion rate (%) | ACR yield (%) |
| Experimental Example 62 | 360 | 701 | 5.7 | 99.9 | 62.3 | 99.8 | 66.5 |
| Experimental Example 63 | 360 | 1,400 | 2.8 | 100.0 | 59.8 | 100.0 | 70.4 |
| Experimental Example 64 | 390 | 701 | 5.7 | 100.0 | 35.4 | 100.0 | 54.8 |
| Experimental Example 65 | 390 | 2,625 | 1.5 | 100.0 | 66.2 | 100.0 | 66.3 |
| Experimental Example 66 | 420 | 2,625 | 1.5 | 100.0 | 53.2 | 100.0 | 53.3 |
| Experimental Example 67 | 420 | 5,250 | 0.76 | 100.0 | 54.8 | 99.8 | 52.3 |
| Experimental Example 68 | 450 | 5,250 | 0.76 | 100.0 | 56.1 | 100.0 | 45.1 |
| Experimental Example 69 | 450 | 10,500 | 0.38 | 100.0 | 59.0 | 99.6 | 35.7 |
| Experimental Example 61 | 300 | 701 | 5.7 | 93.9 | 61.5 | 55.8 | 22.8 |
| Experimental Example 70 | 480 | 10,500 | 0.38 | 100.0 | 0.0 | 100.0 | 3.5 |
| Experimental Example 71 | 390 | 161 | 5.7 | 100.0 | 11.1 | 100.0 | 25.3 |

GLY feed amount: feed amount of glycerin gas per 1 L of catalyst
GLY: glycerin
ACR: acrolein From Table 10, it is found that if the reaction temperature was in a range of higher than 300° C. and not higher than 450° C., acrolein can be produced at a high yield, even when glycerin feed amount was made high.

INDUSTRIAL APPLICABILITY

According to the present invention, both the energy consumption and the wastewater amount in the production of acrolein from glycerin can be decreased to make small an environmental load. According to the present invention, an excellent yield of acrolein and a prolonged life of a catalyst can also be realized.

According to the present invention in which the feed amount of glycerin per 1 L of a catalyst is from 300 to 15,000 g/hr and the reaction temperature for producing acrolein is from 350° C. to 460° C., a reaction apparatus can be made compact and at the same time a process for producing acrolein with high productivity can be provided.

According to the present invention in which the pressure at the inlet of a reactor is not lower than 1 kPa and not higher than 90 kPa, acrolein can be produced at a high yield and at a low cost, even if water is not allowed to be contained in a raw material gas.

According to the present invention in which a raw material gas contains a fatty acid and/or a fatty acid ester and the total amount of the fatty acid and the fatty acid ester is from 0.001% to 5% by mass, relative to glycerin gas, acrolein can be produced with high efficiency.

The invention claimed is:

1. A process for producing acrolein by bringing a raw material gas containing glycerin gas into contact with a solid acid catalyst in a reactor, wherein a partial pressure of the glycerin gas in the raw material gas is from 0.01 to 30 kPa, and wherein the raw material gas comprises water vapor as a condensable gas and a partial pressure of the water vapor is at most 5 times higher than the partial pressure of the glycerin gas.

2. The process for producing acrolein according to claim 1, wherein a space velocity (GHSV) of the glycerin gas is from 70 to 2,400 hr$^{-1}$.

3. The process for producing acrolein according to claim 1, wherein a feed amount of the glycerin gas per 1 L of the catalyst is from 300 to 15,000 g/hr.

4. The process for producing acrolein according to claim 1, wherein a reaction temperature for producing acrolein is from 350° C. to 460° C.

5. The process for producing acrolein according to claim 1, wherein a reaction temperature for producing acrolein is higher than 300° C. and not higher than 450° C.

6. The process for producing acrolein according to claim 1, wherein a pressure at an inlet of the reactor is higher than 90 kPa and a contact time calculated by dividing a volume of the catalyst by a flow rate of the raw material gas per 1 second is from 0.1 to 7.2 seconds.

7. The process for producing acrolein according to claim 1, wherein a pressure at an inlet of the reactor is not lower than 1 kPa and not higher than 90 kPa.

8. The process for producing acrolein according to claim 1, wherein the raw material gas comprises a noncondensable gas and a concentration of the noncondensable gas in the raw material gas at the inlet of the reactor is 10 mol % or lower.

9. The process for producing acrolein according to claim 1, wherein the raw material gas comprises a condensable gas other than the glycerin gas and a concentration of the condensable gas other than glycerin gas at the inlet of the reactor is 60 mol % or lower.

10. The process for producing acrolein according to claim 1, wherein the glycerin gas is generated by setting a temperature of a glycerin evaporator to be 285° C. or lower.

11. The process for producing acrolein according to claim 1, wherein the raw material gas comprises a fatty acid and/or a fatty acid ester and a total mass of the fatty acid and the fatty acid ester is from 0.001% to 5% by mass, relative to the glycerin gas.

12. The process for producing acrolein according to claim 11, wherein the fatty acid is a saturated fatty acid and/or an unsaturated fatty acid, each having from 4 to 22 carbon atoms.

13. The process for producing acrolein according to claim 11, wherein the fatty acid ester is an ester of a saturated fatty acid and/or an unsaturated fatty acid, each having from 4 to 22 carbon atoms, with an alcohol having from 1 to 4 carbon atoms.

14. The process for producing acrolein according to claim 1, wherein the glycerin is produced by hydrolysis or ester exchange of fats and oils.

15. A process for producing acrolein according to claim 4, comprising alternately repeating an acrolein production step (1) for producing acrolein by a process for producing acrolein according to claim 4 and a reactivation step (2) for reactivating a solid acid catalyst having activity decreased in the step (1) by bringing a gas for reactivation containing an oxidizing gas into contact with the solid acid catalyst, wherein a highest temperature Tm(2) in the reactivation step (2) meets $300°\text{C}. \leq Tm(2)$.

16. The process for producing acrolein according to claim 15, wherein an absolute value DT(12) of a difference between a temperature at a time of finishing in the acrolein production step (1) and a temperature at a time of starting in the reactivation step (2) when the acrolein production step (1) is switched to the reactivation step (2) meets $DT(12) \leq 100°\text{C}$.

17. The process for producing acrolein according to claim 15, wherein an absolute value DT(21) of a difference between a temperature at a time of finishing in the reactivation step (2) and a temperature at a time of starting in the acrolein production step (1) when the reactivation step (2) is switched to the acrolein production step (1) meets $DT(21) \leq 100°\text{C}$.

18. The process for producing acrolein according to claim 2, wherein a feed amount of the glycerin gas per 1 L of the catalyst is from 300 to 15,000 g/hr.

19. The process for producing acrolein according to claim 2, wherein a reaction temperature for producing acrolein is from 350° C. to 460° C.

20. The process for producing acrolein according to claim 2, wherein a reaction temperature for producing acrolein is higher than 300° C. and not higher than 450° C.

21. The process for producing acrolein according to claim 2, wherein a pressure at an inlet of the reactor is higher than 90 kPa and a contact time calculated by dividing a volume of the catalyst by a flow rate of the raw material gas per 1 second is from 0.1 to 7.2 seconds.

22. The process for producing acrolein according to claim 4, wherein a pressure at an inlet of the reactor is higher than 90 kPa and a contact time calculated by dividing a volume of the catalyst by a flow rate of the raw material gas per 1 second is from 0.1 to 7.2 seconds.

23. The process for producing acrolein according to claim 5, wherein a pressure at an inlet of the reactor is higher than 90 kPa and a contact time calculated by dividing a volume of the catalyst by a flow rate of the raw material gas per 1 second is from 0.1 to 7.2 seconds.

24. The process for producing acrolein according to claim 19, wherein a pressure at an inlet of the reactor is higher than 90 kPa and a contact time calculated by dividing a volume of the catalyst by a flow rate of the raw material gas per 1 second is from 0.1 to 7.2 seconds.

25. The process for producing acrolein according to claim 20, wherein a pressure at an inlet of the reactor is higher than 90 kPa and a contact time calculated by dividing a volume of the catalyst by a flow rate of the raw material gas per 1 second is from 0.1 to 7.2 seconds.

26. The process for producing acrolein according to claim 2, wherein a pressure at an inlet of the reactor is not lower than 1 kPa and not higher than 90 kPa.

27. The process for producing acrolein according to claim 4, wherein a pressure at an inlet of the reactor is not lower than 1 kPa and not higher than 90 kPa.

28. The process for producing acrolein according to claim 5, wherein a pressure at an inlet of the reactor is not lower than 1 kPa and not higher than 90 kPa.

29. The process for producing acrolein according to claim 19, wherein a pressure at an inlet of the reactor is not lower than 1 kPa and not higher than 90 kPa.

30. The process for producing acrolein according to claim 20, wherein a pressure at an inlet of the reactor is not lower than 1 kPa and not higher than 90 kPa.

31. The process for producing acrolein according to claim 2, wherein the raw material gas comprises a noncondensable gas and a concentration of the noncondensable gas in the raw material gas at the inlet of the reactor is 10 mol % or lower.

32. The process for producing acrolein according to claim 4, wherein the raw material gas comprises a noncondensable gas and a concentration of the noncondensable gas in the raw material gas at the inlet of the reactor is 10 mol % or lower.

33. The process for producing acrolein according to claim 5, wherein the raw material gas comprises a noncondensable gas and a concentration of the noncondensable gas in the raw material gas at the inlet of the reactor is 10 mol % or lower.

34. The process for producing acrolein according to claim 2, wherein the raw material gas comprises a condensable gas other than the glycerin gas and a concentration of the condensable gas other than glycerin gas at the inlet of the reactor is 60 mol % or lower.

35. The process for producing acrolein according to claim 2, wherein the glycerin gas is generated by setting a temperature of a glycerin evaporator to be 285° C. or lower.

36. The process for producing acrolein according to claim 7, wherein the glycerin gas is generated by setting a temperature of a glycerin evaporator to be 285° C. or lower.

37. The process for producing acrolein according to claim 26, wherein the glycerin gas is generated by setting a temperature of a glycerin evaporator to be 285° C. or lower.

38. The process for producing acrolein according to claim 11, wherein the glycerin is produced by hydrolysis or ester exchange of fats and oils.

39. The process for producing acrolein according to claim 12, wherein the glycerin is produced by hydrolysis or ester exchange of fats and oils.

40. A process for producing acrolein according to claim 5, comprising alternately repeating an acrolein production step (1) for producing acrolein by a process for producing acrolein according to claim 5 and a reactivation step (2) for reactivating a solid acid catalyst having activity decreased in the step (1) by bringing a gas for reactivation containing an oxidizing gas into contact with the solid acid catalyst, wherein a highest temperature Tm(2) in the reactivation step (2) meets $300°\text{C}. \leq Tm(2)$.

41. A process for producing acrolein according to claim 19, comprising alternately repeating an acrolein production step (1) for producing acrolein by a process for producing acrolein according to claim 21 and a reactivation step (2) for reactivating a solid acid catalyst having activity decreased in the step (1) by bringing a gas for reactivation containing an oxidizing gas into contact with the solid acid catalyst, wherein a highest temperature Tm(2) in the reactivation step (2) meets 300° C.≦Tm(2).

42. A process for producing acrolein according to claim 20, comprising alternately repeating an acrolein production step (1) for producing acrolein by a process for producing acrolein according to claim 22 and a reactivation step (2) for reactivating a solid acid catalyst having activity decreased in the step (1) by bringing a gas for reactivation containing an oxidizing gas into contact with the solid acid catalyst, wherein a highest temperature Tm(2) in the reactivation step (2) meets 300° C.≦Tm(2).

43. The process for producing acrolein according to claim 40, wherein an absolute value DT(12) of a difference between a temperature at a time of finishing in the acrolein production step (1) and a temperature at a time of starting in the reactivation step (2) when the acrolein production step (1) is switched to the reactivation step (2) meets DT(12)≦100° C.

44. The process for producing acrolein according to claim 16, wherein an absolute value DT(21) of a difference between a temperature at a time of finishing in the reactivation step (2) and a temperature at a time of starting in the acrolein production step (1) when the reactivation step (2) is switched to the acrolein production step (1) meets DT(21)≦100° C.

45. The process for producing acrolein according to claim 40, wherein an absolute value DT(21) of a difference between a temperature at a time of finishing in the reactivation step (2) and a temperature at a time of starting in the acrolein production step (1) when the reactivation step (2) is switched to the acrolein production step (1) meets DT(21)≦100° C.

46. The process for producing acrolein according to claim 43, wherein an absolute value DT(21) of a difference between a temperature at a time of finishing in the reactivation step (2) and a temperature at a time of starting in the acrolein production step (1) when the reactivation step (2) is switched to the acrolein production step (1) meets DT(21)≦100° C.

\* \* \* \* \*